United States Patent
Berggren et al.

(10) Patent No.: US 10,226,530 B2
(45) Date of Patent: *Mar. 12, 2019

(54) METHODS FOR TREATING AND/OR LIMITING DEVELOPMENT OF DIABETES

(71) Applicant: Biocrine AB, Solna (SE)

(72) Inventors: Per Olof Berggren, Solna (SE); Shao-Nian Yang, Stockholm (SE)

(73) Assignee: BioCrine AB, Solna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/660,340

(22) Filed: Jul. 26, 2017

(65) Prior Publication Data

US 2017/0333555 A1    Nov. 23, 2017

Related U.S. Application Data

(60) Continuation of application No. 14/995,341, filed on Jan. 14, 2016, now Pat. No. 9,744,232, which is a division of application No. 14/717,903, filed on May 20, 2015, now Pat. No. 9,353,183, which is a division of application No. 14/026,145, filed on Sep. 13, 2013, now Pat. No. 9,068,973, which is a continuation of application No. 13/532,601, filed on Jun. 25, 2012, now Pat. No. 8,557,513.

(60) Provisional application No. 61/501,480, filed on Jun. 27, 2011.

(51) Int. Cl.

| | | |
|---|---|---|
| *A61K 38/00* | (2006.01) | |
| *A61K 31/47* | (2006.01) | |
| *A61K 39/395* | (2006.01) | |
| *C07K 16/28* | (2006.01) | |
| *G01N 33/50* | (2006.01) | |
| *A61K 31/472* | (2006.01) | |
| *A61K 31/496* | (2006.01) | |
| *A61K 31/7076* | (2006.01) | |
| *A61K 31/713* | (2006.01) | |
| *C12N 15/113* | (2010.01) | |
| *C12N 15/115* | (2010.01) | |

(52) U.S. Cl.
CPC .......... *A61K 39/395* (2013.01); *A61K 31/472* (2013.01); *A61K 31/496* (2013.01); *A61K 31/7076* (2013.01); *A61K 31/713* (2013.01); *C07K 16/2842* (2013.01); *C12N 15/113* (2013.01); *C12N 15/115* (2013.01); *C12N 15/1138* (2013.01); *G01N 33/507* (2013.01); *G01N 33/5041* (2013.01); *C12N 2310/14* (2013.01); *C12N 2320/30* (2013.01)

(58) Field of Classification Search
None
See application file for complete search history.

(56) References Cited

U.S. PATENT DOCUMENTS

| | | |
|---|---|---|
| 8,030,288 B2 | 10/2011 | Berggren et al. |
| 8,084,439 B2 | 12/2011 | Berggren et al. |
| 2002/0094956 A1 | 7/2002 | Cosgrove |
| 2004/0224304 A1 | 11/2004 | Berggren |
| 2009/0060843 A1 | 3/2009 | Berggren et al. |
| 2011/0244509 A1 | 10/2011 | Berggren et al. |

FOREIGN PATENT DOCUMENTS

| | | |
|---|---|---|
| WO | 2000/027422 | 5/2000 |
| WO | 2003/006893 | 1/2003 |
| WO | 2006/047759 | 5/2006 |

OTHER PUBLICATIONS

Cejvan et al., Diabetes 52:1176-1181 (2003).
Zambre et al., Biochem. Pharmacol. 57:1159-1164 (1999).
Fagan et al., Surgery 124:254-259 (1998).
Atzmon, G., et al. (2006). Lipoprotein genotype and conserved pathway for exceptional longevity in humans. PLoS Biol. 4, e113.
Bosco, D., et al. (2000). Importance of cell-matrix interactions in rat islet β-cell secretion in vitro: role of α6β1 integrin. Diabetes 49, 233-243.
Catterall, W.A. (2000). Structure and regulation of voltage-gated Ca1+ channels. Annu. Rev. Cell Dev. Biol. 16, 521-555.
Chan, D.C., et al. (2002). Apolipoprotein B-100 kinetics ill visceral obesity: associations with plasma apolipoprotein C-III concentration. Metabolism 51, 1041-1046.
Clayey, V., et al. (1995). Modulation of lipoprotein B binding to the LDL receptor by exogenous lipids and apolipoproteins CI, CII, CIII, and E Arterioscler. Thromb. Vasc. Biol. 15,963-971.
Fang, D.Z., et al. (2000). Apolipoprotein C-III can specifically bind to hepatic plasma membranes. Mol. Cell. Biochem. 207, 57-64.
Gangabadage, C.S., et al. (2008). Structure and dynamics of human apolipoprotein CIII J. Biol. Chem. 283, 17416-17427.
Gui, P., et al. (2006). Integrin receptor activation triggers converging regulation of Cavl.2 calcium channels by c-Src and protein kinase A pathways. J. Biol. Chem. 281, 14015-14025.
Huard, K., et al. (2005). Apolipoproteins C-II and c-m inhibit selective uptake of low- and bigh-density lipoprotein cholesteryl esters ill HepG2 cells. Int. J. Biochem. Cell Biol. 37, 1308-1318.
Jong, M.C., et al. (1999). Role of ApoCs in lipoprotein metabolism: functional differences between ApoCI, ApoC2, and ApoC3. Arterioscler. Thromb. Vasco Biol. 19, 472-484.
Juntti-Berggren, L., et al. (1993). Increased activity of L-type Ca2+ channels exposed to serum from patients with type I diabetes. Science 261, 86-90.
Juntti-Berggren, L., et al. (2004). Apolipoprotein CIII promotes Ca2+-dependent β cell death in type 1 diabetes. Proc. Natl Acad. Sci USA 101, 10090-10094.
Kantengwa, et al. (1997). Identification and characterization of α3β1 integrin on primary and transformed rat islet cells. Exp. Cell Res. 237, 394-402.

(Continued)

Primary Examiner — Shulamith H Shafer
(74) Attorney, Agent, or Firm — McDonnell Boehnen Hulbert & Berghoff LLP

(57) ABSTRACT

The present invention provides methods for identifying candidate compounds for limiting development of and/or treating diabetes, and methods for limiting development of and/or treating diabetes.

12 Claims, 8 Drawing Sheets

Specification includes a Sequence Listing.

(56) References Cited

OTHER PUBLICATIONS

Kato, S., et al. (1996). Alterations in basal and glucose-stimulated voltage-dependent Ca2+ channel activities in pancreatic β cells of non-insulin-dependent diabetes mellitus GK rats. J. Clin. Invest. 97,2417-2425.

Kawakami, A., et al. (2006). Apolipoprotein CIII in apolipoprotein B lipoproteins enhances the adhesion of human monocytic cells to endothelial cells. Circulation 113, 691-700.

Kawakami, A., et al. (2007). Apolipoprotein CIII-induced THP-I cell adhesion to endothelial cells involves Dertussistoxin-sensitive G protein- and protein kinase Ca-mediated nuclear factor-KB activation. Arterioscler. Thromb. Vasco Biol. 27, 219-225.

Kavalali, E.T., et al. (1997). cAMP-dependent enhancement of dihydropyridine-sensitive calcium channel availability in lippocampal neurons. J. Neurosci 17, 5334-5348.

Luo, RH., et al. (2007). Structural basis of integrin regulation and signaling. Annu. Rev. Immunol. 25, 619-647.

Mukai, E., et al. (2011). Exendin-4 suppresses Src activation and reactive oxygen species production in diabetic Goto-Kakizaki rat islets in an Epac-dependent manner. Diabetes 60, 218-226.

Nikolova, G., et al. (2006). The vascular basement membrane: a niche for insulin gene expression and β cell proliferation. Dev. Cell 10, 397-405.

Ristic., H., et al. (1998). Serum from diabetic BB/W rats enhances calcium currents in primary sensory neurons. J. Neurophysiol. 80, 1236-1244.

Rueckschloss, U., et al. (2004). Contraction augments L-type Ca2+ currents in adherent guinea-pig cardiomyocytes. J. Physiol. 560, 403-411.

Sol, E.M., et al. (2009). Role of MAPK in apolipoprotein CIII-induced apoptosis in INS-IE cells. Lipids Health Dis. 8; 3.

Sundsten, T., et al. (2008). Serum protein patterns in newly diagnosed type 2 diabetes mellitus—influence of diabetic environment and family history of diabetes. Diabetes Metab. Res. Rev. 24, 148-154.

Waitkus-Edwards, K.R, et al. (2002). α4β1 Integrin activation of L-type calcium channels in vascular smooth muscle muses arteriole vasoconstriction. Circ. Res. 90.473-480.

Wu, X., et al. (2001). Regulation of the L-type calcium channel by α5β1 integrin requires signaling between focal adhesion proteins. J. Biol Chem. 276.30285-30292.

Xu, S., et al. (1997). Apolipoproteins of HDL can directly mediate binding to the scavenger receptor SR-BI, anHDL receptor that mediates selective lipid uptake. J. Lipid Res. 38, 1289-1298.

Yang, J.,et al. (1993). Enhancement of N- and L-type calcium channel currents by protein kinase C in frog sympathetic neurons. Neuron 10, 127-136.

Yang, S.N., et al. (2005). β-cell Cav channel regulation in physiology and pathophysiology. Am. J. Physiol 288, EI6-E28.

Yang, S.N., et al. (2006). The role of voltage-gated calcium channels in pancreatic β-cell physiology and pathophysiology. Endocr. Rev. 27, 621-676.

NCBI Accession No. CAA25233, Oct. 7, 2008.

NCBI Accession No. CAA40746, Apr. 28, 1991.

NCBI Accession No. CAA48419, Nov. 14, 2006.

Holmberg, et al., "Lowering apolipoprotein CIII delays onset of type 1 diabetes," Proceedings of the National Academy of Sciences (2011) vol. 108(26), pp. 10685-10689.

Butler et al., "β-cell deficit and increased β-cell apoptosis in Humans with type 2 Diabetes" Diabetes (2003) vol. 52, pp. 102-110.

Holmberg et al. "Lowering apolipoprotein CIII delays onset of type 1 diabetes" PNAS (2011) vol. 108, pp. 1-5.

Hokanson et al. "Susceptibility to type 1 Diabetes is associated with ApoCIII Gene Haplotypes" Diabetes (2006) vol. 55, pp. 834-838.

Wang et al. "Role for β1 Integrin and Its Associated α3, α5, and α6 Subunits in Development of the Human Fetal Pancreas" Diabetes (2006) vol. 54, pp. 2080-2089.

Figure 5
A
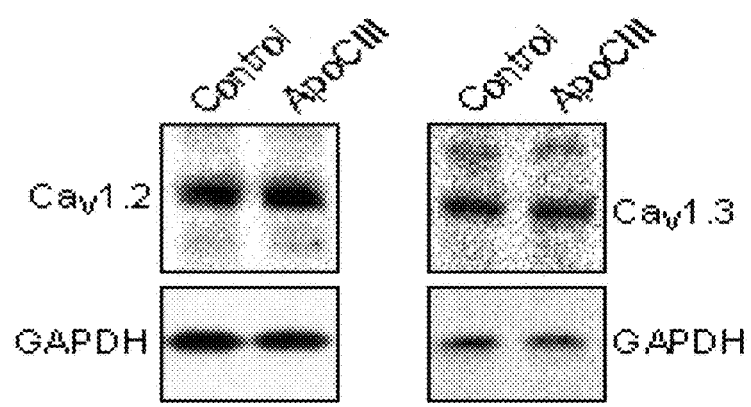
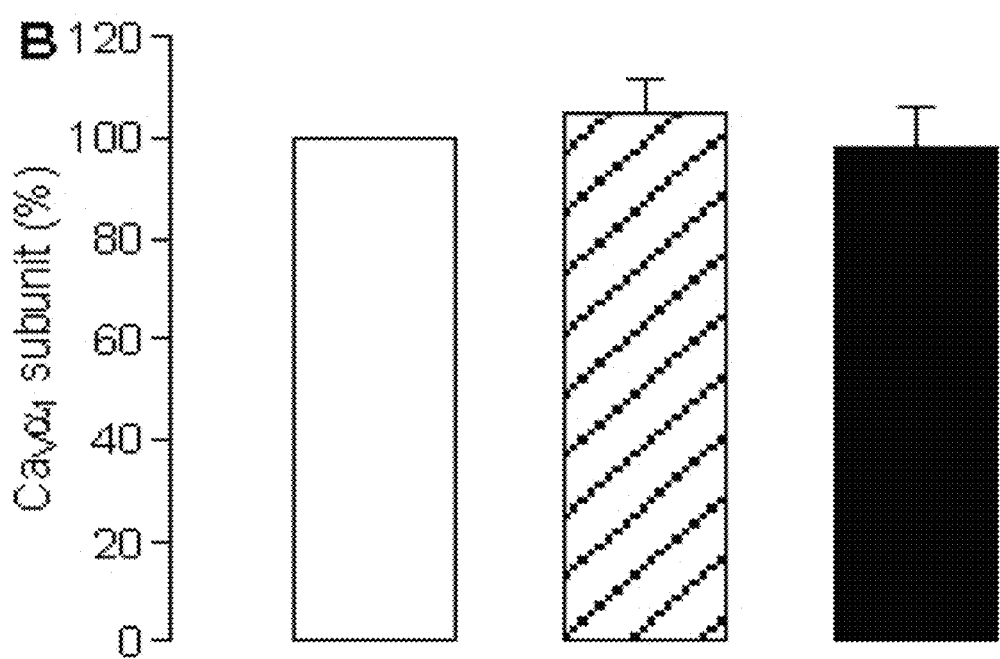

SEQUENCE LISTING

<160> NUMBER OF SEQ ID NOS: 8

<210> SEQ ID NO 1
<211> LENGTH: 487
<212> TYPE: DNA
<213> ORGANISM: Homo sapiens
<220> FEATURE:
<221> NAME/KEY: CDS
<222> LOCATION: (1)..(300)

<400> SEQUENCE: 1

```
atg cag ccc cgg gta ctc ctt gtt gtt gcc ctc ctg gcg ctc ctg gcc      48
Met Gln Pro Arg Val Leu Leu Val Val Ala Leu Leu Ala Leu Leu Ala
1               5                   10                  15 tct gcc cga gct tca gag gcc gag gat gcc tcc ctt ctc agc ttc atg      96
Ser Ala Arg Ala Ser Glu Ala Glu Asp Ala Ser Leu Leu Ser Phe Met
                20                  25                  30 cag ggt tac atg aag cac gcc acc aag acc gcc aag gat gca ctg agc     144
Gln Gly Tyr Met Lys His Ala Thr Lys Thr Ala Lys Asp Ala Leu Ser
            35                  40                  45 agc gtg cag gag tcc cag gtg gcc cag cag gcc agg ggc tgg gtg acc     192
Ser Val Gln Glu Ser Gln Val Ala Gln Gln Ala Arg Gly Trp Val Thr
        50                  55                  60 gat ggc ttc agt tcc ctg aaa gac tac tgg agc acc gtt aag gac aag     240
Asp Gly Phe Ser Ser Leu Lys Asp Tyr Trp Ser Thr Val Lys Asp Lys
65                  70                  75                  80 ttc tct gag ttc tgg gat ttg gac cct gag gtc aga cca act tca gcc     288
Phe Ser Glu Phe Trp Asp Leu Asp Pro Glu Val Arg Pro Thr Ser Ala
                85                  90                  95 gtg gct gcc tga gacctcaata ccccaagtcc acctgcctat ccatcctgcc         340
Val Ala Ala agctccttgg gtcctgcaat ctccagggct gcccctgtag gttgcttaaa agggacagta   400
ttctcagtgc tctcctaccc cacctcatgc ctggcccccc tccaggcatg ctggcctccc   460
aataaagctg gacaagaagc tgctatg                                       487
```

<210> SEQ ID NO 2
<211> LENGTH: 99
<212> TYPE: PRT
<213> ORGANISM: Homo sapiens

<400> SEQUENCE: 2

```
Met Gln Pro Arg Val Leu Leu Val Val Ala Leu Leu Ala Leu Leu Ala
1               5                   10                  15

Ser Ala Arg Ala Ser Glu Ala Glu Asp Ala Ser Leu Leu Ser Phe Met
                20                  25                  30

Gln Gly Tyr Met Lys His Ala Thr Lys Thr Ala Lys Asp Ala Leu Ser
            35                  40                  45

Ser Val Gln Glu Ser Gln Val Ala Gln Gln Ala Arg Gly Trp Val Thr
        50                  55                  60

Asp Gly Phe Ser Ser Leu Lys Asp Tyr Trp Ser Thr Val Lys Asp Lys
65                  70                  75                  80

Phe Ser Glu Phe Trp Asp Leu Asp Pro Glu Val Arg Pro Thr Ser Ala
                85                  90                  95

Val Ala Ala
```

<210> SEQ ID NO 3
<211> LENGTH: 2509
<212> TYPE: DNA
<213> ORGANISM: Rattus norvegicus

<400> SEQUENCE: 3

```
taaagagacg gatgacctac agccccaggc ccacccattc aacaggccta gctcattccc      60
aagcccagac atcaaggcat gggacaccca cgcatggcag cttcgtgtcc agctttatta     120
gggacagcat gtttaggtga ggtctgggga gggataaagg catgagaata tactttcccc     180
ttagagcaac cttcggaggc agcaggatag atggccagac acatctggaa catggaggtc     240
tcacggctca agagttggtg ttgttagttg gtcctcaggg ccagactccc agaggccagt     300
gaacttatca gtgaacttgc tccagtagcc tttcagggat ttgaagcgat tgtccatcca     360
gcccctgggg gttaaaacag taataggtgt gtgtgtgtgt gtgtgtgtgt gtgtgtgtgt     420
gtgtgtgtgt gtgtgtgtgt gaaaagatct cctgtgggca gctagaccca ggggtgcacc     480
taggcctcca ctggctccct aagccaccag caccaccta cctagcacca ccctcagaat     540
cacctgcagc taccactcaa ggtggaggag atggtaaagg ctaagaaaac ccaccttcat     600
cagagcccca ttacctcccg tccaatctct cttcaggcct gaggcaccaa ccactgggga     660
ggtggatact aaggtcagct tgcctttgta gtccatagaa acagtgtcct tgaggtgtcc     720
catccctggc tctaagtgga tggatcaagg gaggggtgaa cttctgtttt ggaaacatta     780
ccagagggct tctaagctct gtgatctagg ccaggttatc taactctttc ccagctgcgg     840
aggtagatag tacctctcca caacctgttc tgggcacaga gactgtcaac atcttttgct     900
acataggcaa tgatcaaatg tcacgtaaac gattggcagg gtaatgtttc atcacgggca     960
agatgcctca cttaggttga gcccagggat ggaaacaggg cagaaccccc aacccgtaat    1020
gctcaacctt ccaacttccc tgtaatcaga gcaggaaggc ctcccagagc acaccctaga    1080
ccctgtgctc aaagaagaaa acctgcaggg aggctgaacg ctcctcaggc tgctctgagg    1140
agaagcagag gagatagaag aagtctgctt gcactgcctg tcatcttagt cacagtcccc    1200
agcaaaggcc ccgtgagaga ctggatgctc agacgggccc aagaccctgg taaacttggt    1260
gggccacagt ctccgtgtcc agggcctcag caccagggca ggaggggcga ggaccaggaa    1320
aggaggtccg tgtgcatacc tggccaccac agctatatca gactcctgca tgctgcttag    1380
tgcatcctgg accgtcttgg aggcttgttc catgtagccc tgcatagagc ccagcagcaa    1440
ggatccctct ccctcatcag ctcctgcaag agagcagagt tgagccaggc cagccctcag    1500
ctcttgccca gccatcgctt ttcagggtag ggtcccagaa ccagctcccg cagaaatccc    1560
agccccactt ccaccagctt acgggcagag gccaggagag ccacgagggc cacgatgagg    1620
agcattcggg gctgcatggc acctgtgcac ctgcgggaga ccatcttgtg agagggtatt    1680
gtggatctcc acatctaagc ccttccctgg agaacaccac ggcccctctg tcatgaatcc    1740
ccaagccttt ctcctactga tatcagctct cggagagaga actaagaaga cccagaccca    1800
ccccaagggg ctggaaggtg gaatgtggga atcctctgca aagcagaaca tctacccagc    1860
ctctgcccca atatatggag aaacaacagg tttcttttttc tctctaggct tcaggctttt    1920
cagtctgggg taggcacgga tatcaaaggc ttctaatagc tcagagcaag acgaacaagg    1980
ggcagcatga cccagttccc aatcagctct gccactaccc agtgcaaggc ttttttgccc    2040
agtggcctcc ctttcctcag cttctagcct ccccacccca ccaggatacc caagggctgg    2100
aggccgtgaa ttccaagcat tctgtaggct agctggctga gtggccagag cgtcttctct    2160
ctgtctcctc cctcccttcc tctcctcccc aggggcatta cctggagtag ctagctgctt    2220
ctagggataa aactgggcag gcaagccggg acgctctgat ctgttttata ttggctccag    2280
```

-continued

| | |
|---|---|
| gatgggacag cgggcacaga aggcccagtg agctggtcaa aggtcacctg ctgaacagtc | 2340 |
| cagaccagag cccgaggcag ggaggccatg cagccagctg ccagaggagt tgagaaatcc | 2400 |
| ctcagagatt gcccacaccg ttcacttcca cctccgcagc caagagatca gctactgacc | 2460 |
| tgcctcgatg agactggtga gacaggaaaa gactcagggg acaagcctt | 2509 |

```
<210> SEQ ID NO 4
<211> LENGTH: 101
<212> TYPE: PRT
<213> ORGANISM: Rattus norvegicus

<400> SEQUENCE: 4
```

Met Gln Pro Arg Met Leu Leu Ile Val Ala Leu Val Ala Leu Leu Ala
1               5                   10                  15

Ser Ala Arg Ala Asp Glu Gly Glu Gly Ser Leu Leu Leu Gly Ser Met
            20                  25                  30

Gln Gly Tyr Met Glu Gln Ala Ser Lys Thr Val Gln Asp Ala Leu Ser
        35                  40                  45

Ser Met Gln Glu Ser Asp Ile Ala Val Val Ala Ser Arg Gly Trp Met
    50                  55                  60

Asp Asn Arg Phe Lys Ser Leu Lys Gly Tyr Trp Ser Lys Phe Thr Asp
65                  70                  75                  80

Lys Phe Thr Gly Leu Trp Glu Ser Gly Pro Glu Asp Gln Leu Thr Thr
                85                  90                  95

Pro Thr Leu Glu Pro
            100

```
<210> SEQ ID NO 5
<211> LENGTH: 3262
<212> TYPE: DNA
<213> ORGANISM: Macaca fascicularis
<220> FEATURE:
<221> NAME/KEY: CDS
<222> LOCATION: (858)..(912)
<220> FEATURE:
<221> NAME/KEY: CDS
<222> LOCATION: (1048)..(1171)
<220> FEATURE:
<221> NAME/KEY: CDS
<222> LOCATION: (2871)..(2988)

<400> SEQUENCE: 5
```

| | |
|---|---|
| ctgcagggct ggcgggacag cagcatggac acagtctcct ggggatttcc caactctccc | 60 |
| gccagcttgc tgcctctggc cgccctgcct caggccctgg tctctgatca gcaggtgacc | 120 |
| tttgcccagt gccctgggtc ctcagtgcct gctgccctgg agacaatata aaacaggctc | 180 |
| agaaccctcc tgcctgcctg ctctgttcat ccctagaggc agctgctcca ggtaatgccc | 240 |
| tctggggagg ggaaagagga ggggaggagg atgaagagga gcaagaggag ctccctgccc | 300 |
| agcccagcca gcaagcctgg agaaacactt gctagagcta aggaagcctc ggagctggac | 360 |
| gggtgccccc aacccctcat cataacctga agaaaatgga ggcccgggag gggtgtcact | 420 |
| tgcccaaagc tacacagggg gtggggctgg aaatggttcc aagtgcaggc ttccccgtca | 480 |
| ttctgcaggc ttagggctgg aggaagcctt agacagccca gtcctaccca gacagggaaa | 540 |
| ctgaggcctg gagagggcca gaaagcccca agtcacaca gcatgttggc tgcactggac | 600 |
| agagaccagt ccagaccgca ggtgccttga tgtccagtct ggtgggtttt ctgctccatc | 660 |
| ccacctacct cccctttgggc ccctcactag tcccctttctg agagcccgta ttagcaggaa | 720 |
| gcaggcccct actccctctg gcagaccgag ctcaggtccc accttagggg ccatgccacc | 780 |

| | |
|---|---:|
| tgtccaggga ggggtccaga ggcatggggg cctgggtgc ccctcacagg acaattcctt | 840 |

| | | | | | | | | | | |
|---|---|---|---|---|---|---|---|---|---|---:|
| gcaggaacag aggcgcc | atg | cag | ccc | cgg | gta | ctc | ctt | gtt | gct gcc ctg | 890 |
| | Met | Gln | Pro | Arg | Val | Leu | Leu | Val | Ala Ala Leu | |
| | 1 | | | 5 | | | | | 10 | |

| | | | | | | |
|---|---|---|---|---|---|---:|
| ctg tca ctc ctg gcc tct gcc a | gtaagcactt ggtgggactg ggctggggc | 942 |
| Leu Ser Leu Leu Ala Ser Ala | | |
| 15 | | |

| | |
|---|---:|
| aggatggagg tggcttgggg atcccagtcc taatgggtgg tcaagcagga gctcagggct | 1002 |

| | | | | |
|---|---|---|---|---:|
| cgcctagagg ccgatccacc actctcagcc ctgctctttc ctcag | ga | gct tca gag | 1058 |
| | | Arg Ala Ser Glu | |
| | | 20 | |

| | | | | | | | | | | | | | |
|---|---|---|---|---|---|---|---|---|---|---|---|---|---:|
| gcc | gag | gac | acc | tcc | ctt | ctt | ggc | ttc | atg | cag | ggc tac atg cag cat | 1106 |
| Ala | Glu | Asp | Thr | Ser | Leu | Leu | Gly | Phe | Met | Gln | Gly Tyr Met Gln His | |
| | 25 | | | | 30 | | | | | 35 | | |

| | | | | | | | | | | | | | |
|---|---|---|---|---|---|---|---|---|---|---|---|---|---:|
| gcc | acc | aag | acc | gcc | aag | gat | gca | ctg | acc | agc | gtc cag gag tcc cag | 1154 |
| Ala | Thr | Lys | Thr | Ala | Lys | Asp | Ala | Leu | Thr | Ser | Val Gln Glu Ser Gln | |
| | 40 | | | | 45 | | | | 50 | | | |

| | | | | | | | |
|---|---|---|---|---|---|---|---:|
| gtg | gcc | cag | cag | gcc | ag | gtacaccgc tggcctccct ccccatccct | 1201 |
| Val | Ala | Gln | Gln | Ala | Arg | | |
| 55 | | | | 60 | | | |

| | |
|---|---:|
| catgccagct ccctccattc caccgccc tgccctggtg agatcccagc aatggaatgg | 1261 |
| aggtgccagc ctcccctggt cctgtgcctc tttggcctcc tctttcctca cagggccttg | 1321 |
| gtcaggctgc tgtgggagag acgacagagt tgagactgcg ttcccccgg gtccctcctt | 1381 |
| tctcccagag cagttctagg gtgggccatt ttagccctca tttccatttt cctttccttt | 1441 |
| tctttctttt tcttttcttt tttttctttt ctttcttttt tttttttgag atggagtctc | 1501 |
| cctctgtcac ccaggctaga gtgcagtggt gcgatctcag cggatctcgg ctcactgcaa | 1561 |
| cctctgcctc ccaggttcac cccattctcc tgcctcagcc tcccaagtag ctgggattac | 1621 |
| aggcgtgcca ccacatccag ctactttttg tattttctc agagacgggg tttccccatg | 1681 |
| ttggacaggc tggtcttgaa ctcctgacct caggtgatct gcctacctcg gcctcccaaa | 1741 |
| ttgctgggat tacaggcatg agccactgcg cctgaccca ttttcctttt ctgaaggtct | 1801 |
| ggctagagca gaggtcctca accttttttgg caccagggac cagttttgtg gtagacagtt | 1861 |
| tttccatggg tcagcgggga tggcttgggg atgaaactgc tccacctcag atcaccaggc | 1921 |
| attggattct cctaagaagc cctccacccc gacccctggc atgcgcagtt cacaacaggt | 1981 |
| ttcacactcc tgtgagaatc taatgccgcc taacctgaca gaaggcgggg cttgggcggt | 2041 |
| attcctctgt cacccatcac tcactttgtg ctgtgcagcc tggctcctaa ctggccatgg | 2101 |
| accagtaccc atctgtgact tgggggctgg ggaccccctgg gctaggggtt tgccttggga | 2161 |
| ggccccacct ggcccaattc tagcctgggt atgagagtgc ttctgctttg ttccaagacc | 2221 |
| tggggccagg gtgagtagaa gtgtgtcctt cctctcccat cctgcccctg cccatcggtc | 2281 |
| ctctcctctc cctactccct tcccaccctc accctgactg gcattggctg gcatagcaga | 2341 |
| ggttgtttat aagcattctt aatcctcaga accggctttg gggtaggtgt tattttccca | 2401 |
| ctttgcagat gagaaaattg aggctcagag cgattaggtg acctgcccca gatcacacaa | 2461 |
| ctaatcaatc ctccaatgac tttccaaatg agaggtcgcc tccctctgtc ctaccctgct | 2521 |
| cggaaccacc aggatataca actccagggg atactgtctg cacagaaaac aatgacagcc | 2581 |
| ttgaccttct catctccccc accctgtcac tctgtgcctc aagcccaggg gcaaaaacat | 2641 |
| ctgaggtcac ctggagacgg cagggttcga cttgtgctgg ggttcctgta agggcatctc | 2701 |

```
ttctcccagg gtggcagctg tgggcagtcc tgcctgaggt ctcagggctg ttgtccagtg    2761
aagttgagag gtggcaggg agagccagtg gggacatggg tgtgggtccc atagttgcct     2821
ccaaaggagt tctcatgccc tgctctgttg cttcccctta ctgatttag a ggc tgg      2877
                                                        Gly Trp gtg acc gat ggc ttc agt tcc ctg aaa gac tac tgg agc acc gtt aag      2925
Val Thr Asp Gly Phe Ser Ser Leu Lys Asp Tyr Trp Ser Thr Val Lys
           65                  70                  75 gac aag tta tct ggg ttc tgg gat ttg aac cct gag gcc aaa ccc act      2973
Asp Lys Leu Ser Gly Phe Trp Asp Leu Asn Pro Glu Ala Lys Pro Thr
 80                  85                  90 ctg gct gag gct gcc tgagacctca atacccccaag tccacctgcc tgtccatcct    3028
Leu Ala Glu Ala Ala
 95 gccagctcct tgggtcctgc agcctccagg gctgccctg taggttgctt aaaagggaca    3088 gtattctcag tgccctccta ccgcacctca tgcctggccc ccctccaggc agggtgtcct    3148 cccaataaag ctggacaaga agctgctatg agtgggccgt cacaagtgtg ccatctgtgt    3208 ctgggtatgg gaaagggtcc gaggctgttc tgtgggtagg cactggacga ctgc          3262
```

<210> SEQ ID NO 6
<211> LENGTH: 99
<212> TYPE: PRT
<213> ORGANISM: Macaca fascicularis

<400> SEQUENCE: 6

```
Met Gln Pro Arg Val Leu Leu Val Ala Ala Leu Leu Ser Leu Leu Ala
  1               5                  10                  15

Ser Ala Arg Ala Ser Glu Ala Glu Asp Thr Ser Leu Leu Gly Phe Met
             20                  25                  30

Gln Gly Tyr Met Gln His Ala Thr Lys Thr Ala Lys Asp Ala Leu Thr
         35                  40                  45

Ser Val Gln Glu Ser Gln Val Ala Gln Gln Ala Arg Gly Trp Val Thr
     50                  55                  60

Asp Gly Phe Ser Ser Leu Lys Asp Tyr Trp Ser Thr Val Lys Asp Lys
 65                  70                  75                  80

Leu Ser Gly Phe Trp Asp Leu Asn Pro Glu Ala Lys Pro Thr Leu Ala
                 85                  90                  95

Glu Ala Ala
```

<210> SEQ ID NO 7
<211> LENGTH: 2411
<212> TYPE: DNA
<213> ORGANISM: Mus musculus
<220> FEATURE:
<221> NAME/KEY: CDS
<222> LOCATION: (54)..(350)

<400> SEQUENCE: 7

```
gctacatcag gggctgtgca gcgtcgccca tactccgagc aaagaactgt ggc cag       56
                                                         Gln
                                                          1 agg cag tcg agg tta gtg agg act gcg agg cag aca ctt tgc tgt gtt     104
Arg Gln Ser Arg Leu Val Arg Thr Ala Arg Gln Thr Leu Cys Cys Val
         5                   10                  15 caa atc caa gtc aag ggt aca aaa atg cag agc aat aaa gcc ttt aac     152
Gln Ile Gln Val Lys Gly Thr Lys Met Gln Ser Asn Lys Ala Phe Asn
     20                  25                  30 ttg gag aag cag aat cat act cca agg aag cat cat cag cat cac cac     200
```

| | | | | | | | | | | | | | | |
|---|---|---|---|---|---|---|---|---|---|---|---|---|---|---|
| Leu | Glu | Lys | Gln | Asn | His | Thr | Pro | Arg | Lys | His | Gln | His | His | His |
| | 35 | | | | 40 | | | | 45 | | | | | |

| cag | cac | cat | cag | cag | caa | cag | cag | cag | cag | cag | caa | cag | cca | ccc | 248 |
|---|---|---|---|---|---|---|---|---|---|---|---|---|---|---|---|
| Gln | His | His | Gln | Gln | Gln | Gln | Gln | Gln | Gln | Gln | Gln | Gln | Pro | Pro | |
| 50 | | | | | 55 | | | | | 60 | | | | 65 | |

| cca | cca | ata | cct | gca | aat | ggc | cag | cag | gcc | agc | agc | cag | aat | gaa | ggc | 296 |
|---|---|---|---|---|---|---|---|---|---|---|---|---|---|---|---|---|
| Pro | Pro | Ile | Pro | Ala | Asn | Gly | Gln | Gln | Ala | Ser | Ser | Gln | Asn | Glu | Gly | |
| | | | 70 | | | | | 75 | | | | | 80 | | | |

| ttg | act | att | gac | ctg | aag | aat | ttt | agg | aaa | cca | gga | gag | aag | acc | ttt | 344 |
|---|---|---|---|---|---|---|---|---|---|---|---|---|---|---|---|---|
| Leu | Thr | Ile | Asp | Leu | Lys | Asn | Phe | Arg | Lys | Pro | Gly | Glu | Lys | Thr | Phe | |
| | | | 85 | | | | | 90 | | | | | 95 | | | |

| aca | cag | cgtagccgtc tctttgtggg caatcttccc cctgatatca ctgaggagga | 400 |
|---|---|---|---|
| Thr | Gln | | |

| aatgaggaaa ctatttgaga aatatggaaa agcaggcgaa gttttcattc ataaggataa | 460 |
|---|---|
| aggctttggc tttattcgct tggaaacacg aaccctagcg gaaattgtca agtggagct | 520 |
| ggacaacatg cccctccgtg ggaagcagct gcgagtgcgc ttcgcctgtc acagtgcatc | 580 |
| ccttacagtc cgcaaccttc ctcagtacgt gtcgaacgac tgctggaag aagcctttc | 640 |
| tgtgttcggc caggtggaga gggctgtagt cattgtggat gaccgaggaa ggccctcagg | 700 |
| gaaaggcatt gttgagttct cagggaagcc agctgctcgg aaagctctgg acagatgcag | 760 |
| tgaaggctcc ttcttgctga ctacatttcc ttggcctgtg actgtggagc ctatggacca | 820 |
| gttagatgat gaagagggac ttccagaaa actggttata aaaaccagc aattccacaa | 880 |
| ggagagagaa cagccaccca gatttgcaca acctggctcc tttgagtatg agtatgccat | 940 |
| gcgctggaag gcactcattg agatggaaa gcaacagcag gatcaagtgg atcggaacat | 1000 |
| caaggaggct cgtgagaagc tggagatgga gatggaggct gcacgtcatg agcaccaggt | 1060 |
| tatgctaatg aggcaggatt tgatgagacg tcaagaagag cttcggagaa tggaggagct | 1120 |
| gcataaccaa gaggttcaga agcgaaagca gttagaactc aggcaggaag aggaacgcag | 1180 |
| gcgccgtgag gaagagatgc ggcgacaaca agaggaaatg atgcgccgac agcaggaagg | 1240 |
| attcaaggga accttccctg atgcgagaga acaagagata cggatgggcc aaatggctat | 1300 |
| gggaggtgct atgggcataa acaatagagg cgcgatgccc cctgctcctg tgccacctgg | 1360 |
| tactccagct cctccaggac ctgccactat gatgccagat ggaacccttg gattgacccc | 1420 |
| accaacaact gaacgtttg gccaagctgc aacaatggaa ggaattggag caattggtgg | 1480 |
| aactcctcct gcattcaacc gtccagctcc gggagctgaa tttgctccaa ataaacgccg | 1540 |
| ccgatattag ataaagttgc attgtctagt ttcctgcagc ccttaaaaga agggccctt | 1600 |
| ttggactagc cagaattcta ccctggaaaa gtgttagggg ttcttcccaa tagataggcc | 1660 |
| ttccctgctt gtactactct agggatcatg cttgaagtca gaggggcaga gaaggggtgg | 1720 |
| tattcaacaa gtcaaagtct gtggtatatt gctttatcaa gactgtctgg tgcattcctg | 1780 |
| aactatatta attgttgagg gcctggagaa ccatgggaaa atgaactcag agctccatta | 1840 |
| atcttgatca ttccttctct ctctttctct ctctcttgtt ttaattactt tctcatcttt | 1900 |
| attcccctca accctgaga cactgccata taccacaa accataaaca tcctccaatg | 1960 |
| acctagcccc atccctccat tcactcccag gtaagaattc agacaaatgt ccacagaggt | 2020 |
| tacagcatac gtacggttgt gttatatctc atatatgacc ccttcatgtc ctaaggaaga | 2080 |
| cattttctct tagaggtttt cattttagta tatcttaaaa gaatcttgtg ttaccttgcc | 2140 |
| tccatctttt tcttgggtaa ggactacact ttgtgtctct gatgttgctg ttcacagctt | 2200 |
| ttcttgatag gcctagtaca atcttgggaa cagggttgct gtgtggtgaa ggtctgacag | 2260 |

```
tagttcttag tcttgcctat cttaggtagc tacgctgtgc atttttattg gtatactatg    2320
aattgttcca gataccttca gtttggaaag ttttctgaga aatggagacg tcatgcggca    2380
tcaccttatt aaaatgcatt tgaagccttt t                                   2411
```

<210> SEQ ID NO 8
<211> LENGTH: 99
<212> TYPE: PRT
<213> ORGANISM: Mus musculus

<400> SEQUENCE: 8

```
Gln Arg Gln Ser Arg Leu Val Arg Thr Ala Arg Gln Thr Leu Cys Cys
1               5                   10                  15

Val Gln Ile Gln Val Lys Gly Thr Lys Met Gln Ser Asn Lys Ala Phe
            20                  25                  30

Asn Leu Glu Lys Gln Asn His Thr Pro Arg Lys His His Gln His His
        35                  40                  45

His Gln Gln His His Gln Gln Gln Gln Gln Gln Gln Gln Gln Gln Pro
    50                  55                  60

Pro Pro Pro Ile Pro Ala Asn Gly Gln Gln Ala Ser Ser Gln Asn Glu
65                  70                  75                  80

Gly Leu Thr Ile Asp Leu Lys Asn Phe Arg Lys Pro Gly Glu Lys Thr
                85                  90                  95

Phe Thr Gln
```

METHODS FOR TREATING AND/OR LIMITING DEVELOPMENT OF DIABETES

CROSS-REFERENCE

This application is a continuation of U.S. application Ser. No. 14/995,341 filed Jan. 14, 2016, which is a divisional of U.S. application Ser. No. 14/717,903 filed May 20, 2015, now U.S. Pat. No. 9,353,183 issued on May 31, 2016, which is a divisional of Ser. No. 14/026,145 filed Sep. 13, 2013, now U.S. Pat. No. 9,068,973 issued Jun. 30, 2015, which is a continuation of U.S. application Ser. No. 13/532,601 filed Jun. 25, 2012, now U.S. Pat. No. 8,557,513 issued on Oct. 15, 2013, which claims priority to U.S. Provisional Patent Application Ser. No. 61/501,480 filed Jun. 27, 2011, each incorporated by reference herein in its entirety.

INTRODUCTION

Voltage-gated calcium ($Ca_V$) channels are critical in β cell physiology and pathophysiology. They are not only take center stage in the regulation of insulin secretion, but are also involved in β cell development, survival and growth through the regulation of protein phosphorylation, gene expression and the cell cycle. The function and density of β cell $Ca_V$ channels are regulated by a wide range of mechanisms either shared by other cell types or specific to β cells, e.g., channel phosphorylation, interaction with other molecules and glucose metabolism-derived signaling. Dysfunctional $Ca_V$ channels causes β cell malfunction and even death as manifested in the most common metabolic disorder diabetes mellitus. Indeed, a T-lymphocyte-mediated autoimmune attack plays a crucial role in β cell death in type 1 diabetes. In addition, factors in type 1 diabetic serum compel unphysiological amounts of $Ca^{2+}$ to enter pancreatic β cells through hyperactivation of β cell $Ca_V$ channels resulting in β cell apoptosis. Undoubtedly, this process aggravates the disease development on top of the autoimmune attack. Such factors are also visualized in type 2 diabetic serum where they behave in the same way as they do in type 1 diabetic serum. In fact, reduction in β cell mass and hyperactivation of β cell $Ca_V$ channels appear under type 2 diabetic conditions such as those in the Goto-Kakizaki rat.

It has been demonstrated that elevated apolipoprotein CIII (ApoCIII) acts as a diabetogenic serum factor to drive β cell destruction via hyperactivation of β cell $Ca_V$ channels. Moreover, we have recently shown that in vivo suppression of ApoCIII delays onset of diabetes in the BioBreeding™ rat. Normally, ApoCIII is a blood plasma component. It is synthesized predominantly in the liver and to a minor extent in the intestine. Liver and intestinal cells release this apolipoprotein into the blood where it is situated on the surface of chylomicrons, very low density lipoproteins (LDLs) and high density lipoproteins (HDLs). ApoCIII is composed of 79 amino acid residues that form six amphiphilic α-helices, each containing about 10 residues. The three-dimensional NMR structure and dynamics of ApoCIII have been resolved when it complexes with sodium dodecyl sulfate micelles, mimicking its natural lipid-bound state. The six amphiphilic α-helices assemble into a necklace-like chain wrapping around the sodium dodecyl sulfate micelle surface. Dogmatically, ApoCIII serves as an effective inhibitor of triglyceride hydrolysis by inhibiting lipoprotein lipase and through interference with triglyceride-rich lipoproteins binding to the negatively charged cell surface where lipoprotein lipases and lipoprotein receptors reside. It impedes the selective uptake of cholesteryl esters from LDL and HDL by binding to the scavenger receptor class B type 1 (SR-BI), and hampers the endocytosis of cholesterol-rich LDL by prevention of apolipoprotein B binding to LDL receptors. Elevated plasma ApoCIII concentration is a feature of dyslipidemia in obesity and observed in both type 1 and type 2 diabetes, whereas a group of Ashkennazi Jewish with reduced plasma ApoCIII concentration maintains cardiovascular health and greater insulin sensitivity with age and reaches exceptional longevity.

In addition to the dogmatic roles in lipid metabolism, ApoCIII is also a multifaceted player in cell signaling. It can bind to distinct cell surface receptors including scavenger receptor class B type 1 (SR-BI), Toll-like receptor 2 (TLR2) and uncharacterized binding sites relaying corresponding signals to their downstream effectors, e.g., β1 integrin, pertussis toxin-sensitive G proteins, NF-κB and protein kinases. However, nothing is known about molecular mechanisms whereby ApoCIII hyperactivates β cell $Ca_V$ channels.

SUMMARY OF THE INVENTION

In a first aspect, the present invention provides methods identifying candidate compounds for limiting development of and/or treating diabetes, comprising
a) contacting a first population of insulin secreting cells with an amount of apolipoprotein CIII (ApoCIII) effective to increase density and/or conductivity of $Ca_v1$ channels, in the presence of one or more test compounds; and
b) identifying those positive test compounds that inhibit an ApoCIII-induced increase in density and/or conductivity of $Ca_v1$ channels in the first population of insulin secreting cells compared to control, wherein the positive test compounds are candidate compounds for limiting development of and/or treating diabetes.

In one embodiment, the control comprises contacting a control population of insulin secreting cells with an amount of apolipoprotein CIII (ApoCIII) effective to increase density and/or conductivity of $Ca_v1$ channels, in the absence of one or more test compounds. This embodiment, which can be combined with the use of any of the other controls disclosed herein unless the context clearly dictates otherwise, may comprise, for example, contacting the control population of cells with a formulation, such as a buffer, that is similar to or identical to the formulation the test compounds are dissolved in.

In another embodiment, the control comprises contacting a control population of insulin secreting cells with an amount of ApoCIII effective to increase density and/or conductivity of $Ca_v1$ channels, in the presence of the one or more test compounds, and further contacting the control population of insulin secreting cells with $Ca_v2$ and/or $Ca_v3$ channel blockers, wherein positive test compounds that inhibit the ApoCII-induced increase in density and/or conductivity of $Ca_v1$ channels in the $Ca_v2$ and/or $Ca_v3$ channel blocker control population of insulin secreting cells to a greater degree than in the first population of insulin secreting cells are candidate compounds for limiting development of and/or treating diabetes.

In another embodiment, the control comprises contacting a control population of insulin secreting cells with an amount of ApoCIII effective to increase density and/or conductivity of $Ca_v1$ channels, in the presence of the one or more test compounds, and further contacting the second population of insulin secreting cells with a Src kinase inhibitor and/or a protein kinase A (PKA) inhibitor, wherein positive test compounds that inhibit the ApoCIII-induced increase in density and/or conductivity of $Ca_v1$ channels in the first population of insulin secreting cells to a greater degree than in the Src kinase inhibitor and/or a protein kinase A (PKA) inhibitor control population of insulin secreting cells are candidate compounds for limiting development of and/or treating diabetes.

In a further embodiment, the control comprises contacting a control population of insulin secreting cells with an amount of ApoCIII effective to increase density and/or conductivity of $Ca_v1$ channels, in the presence of the one or more test compounds, and further contacting the control population of insulin secreting cells with a molecule that inhibits β1 integrin expression or activity, wherein positive test compounds that inhibit the ApoCIII-induced increase in density and/or conductivity of $Ca_v1$ channels in the first population of insulin secreting cells to a greater degree than in the β1 integrin expression or activity control population of insulin secreting cells are candidate compounds for limiting development of and/or treating diabetes.

As will be understood by those of skill in the art, a single control can be used in carrying out the methods of the invention, including but not limited to any of the controls disclosed above. Alternatively, multiple control embodiments can be used (2, 3, or more, including but not limited to any of the controls disclosed above), wherein each embodiment utilizes a different control cell population.

In a second aspect, the present invention provides methods for identifying candidate compounds for limiting development of and/or treating diabetes, comprising
(a) contacting a first population of insulin secreting cells with an amount of ApoCIII effective to increase density and/or conductivity of $Ca_v1$ channels, in the presence of one or more test compounds; and
(b) identifying those positive test compounds that inhibit β1 integrin expression or activity in the first population of insulin secreting cells compared to control, wherein the positive test compounds are candidate compounds for limiting development of and/or treating diabetes.

In one embodiment, the control comprises contacting a second population of insulin secreting cells contacted with an amount of ApoCIII effective to increase density and/or conductivity of $Ca_v1$ channels, in the absence of one or more test compounds. This embodiment may comprise, for example, contacting the second population of cells with a formulation, such as a buffer, that is similar to or identical to the formulation the test compounds are dissolved in.

In a third aspect, the present invention provides methods for identifying candidate compounds for limiting development of and/or treating diabetes, comprising
(a) contacting a first population of insulin secreting cells with an amount of ApoCIII effective to increase density and/or conductivity of $Ca_v1$ channels, in the presence of one or more test compounds; and
(b) identifying those positive test compounds that inhibit activation of PKA and/or Src kinase in the first population of insulin secreting cells compared to control, wherein the positive test compounds are candidate compounds for limiting development of and/or treating diabetes.

In one embodiment, the control comprises contacting a second population of insulin secreting cells contacted with an amount of ApoCIII effective to increase density and/or conductivity of $Ca_v1$ channels, in the absence of one or more test compounds. This embodiment may comprise, for example, contacting the second population of cells with a formulation, such as a buffer, that is similar to or identical to the formulation the test compounds are dissolved in.

In various embodiments of any of these aspects of the invention, each of which can be combined except as clearly dictated otherwise by the context, the method comprises contacting the cells with ApoCIII for at least 6 hours; the candidate compounds are candidate compounds for limiting development of and/or treating type 1 diabetes; and/or wherein the candidate compounds are candidate compounds for limiting development of and/or treating type 2 diabetes.

In a fourth aspect, the present invention provides methods for treating or limiting development of diabetes, comprising administering to a subject in need thereof with an amount effective of an inhibitor of PKA and Src kinase to treat or limit development of diabetes.

In a fifth aspect, the present invention provides methods for treating or limiting development of diabetes, comprising administering to a subject in need thereof with an amount effective of an inhibitor of β1 integrin expression and/or activity. In various embodiments, the inhibitor is selected from the group consisting of an anti-β1 integrin antibody, anti-β1 integrin aptamer, β1 integrin siRNA, β1 integrin shRNA, and β1 integrin antisense oligonucleotides.

In a sixth aspect, the present invention provides methods for treating or limiting development of diabetes, comprising administering to a subject in need thereof with an amount effective of an inhibitor of ApoCIII binding to pancreatic β cells. In various embodiments, the inhibitor is selected from the group consisting of aptamers and antibodies selective for ApoCIII.

DESCRIPTION OF THE FIGURES

FIG. 5. Apolipoprotein CIII incubation does not alter β cell $Ca_V1$ channel expression. (A) Representative immunoblots of RINm5F cell homogenates, subjected to incubation with vehicle as control or apolipoprotein CIII (ApoCIII), probed with anti-$Ca_V1.2$, anti-$Ca_V1.3$ and anti-GAPDH antibodies, respectively. (B) Immunoblot quantification of the relative abundance of $Ca_V1.2$ (hatched column, n=6) and $Ca_V1.3$ subunits (filled column, n=6) in RINm5F cell homogenates subjected to ApoCIII incubation in comparison with control (open column, n=6). There was no significant difference in the relative abundance of total $Ca_V1.2$ and $Ca_V1.3$ subunits between control cells and cells incubated with ApoCIII (P>0.05).

DETAILED DESCRIPTION OF THE INVENTION

Figure 1:
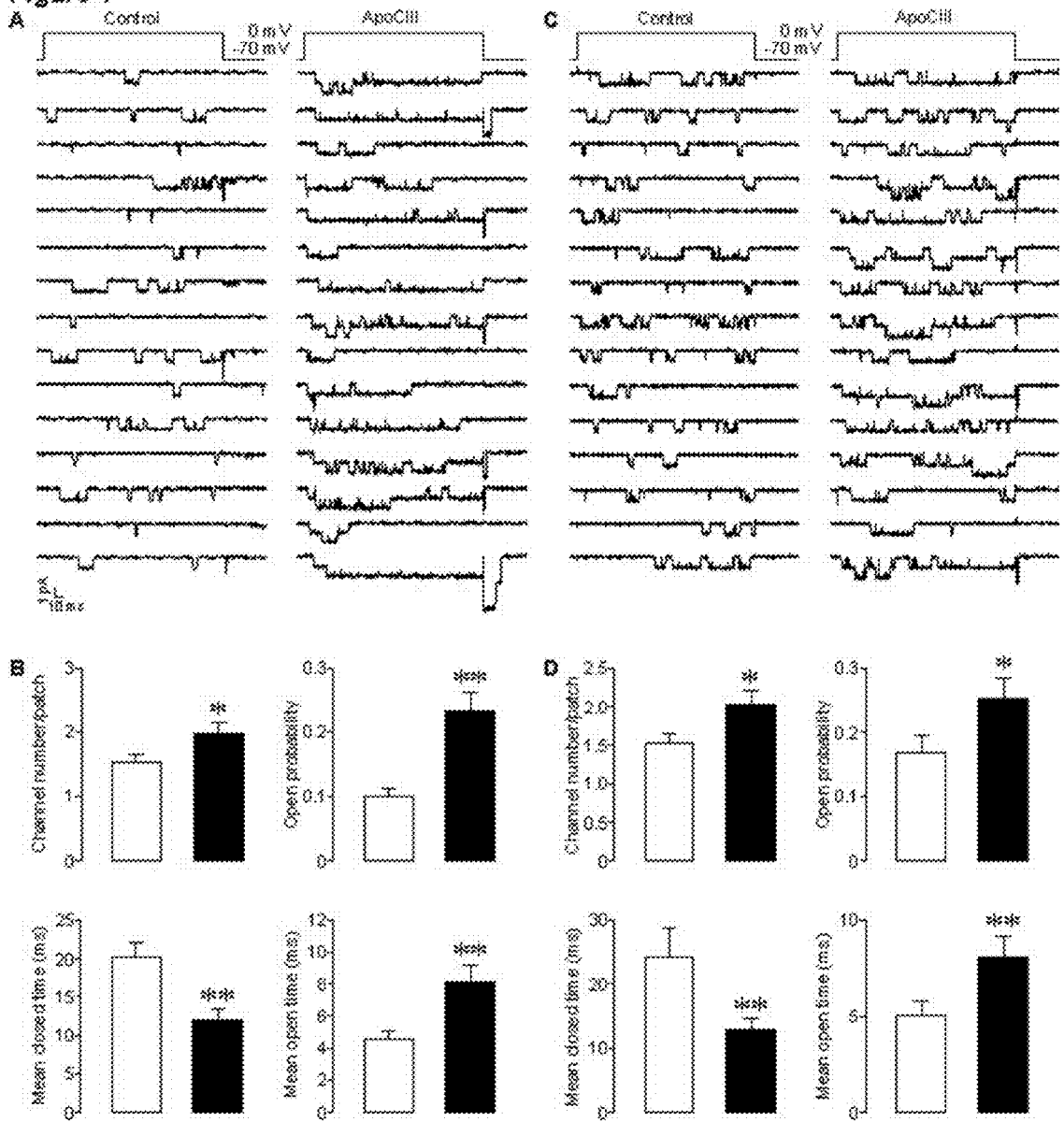
FIG. 1. Apolipoprotein CIII incubation increases both the density and conductivity of $Ca_v1$ channels in β cells. (A) Examples of unitary $Ca_v1$ channel currents detected in plasma membrane patches of mouse islet β cells incubated with either vehicle solution as control or apolipoprotein CIII (ApoCIII). (B) Average number, open probability, mean closed time and mean open time of unitary $Ca_v1$ channels measured in plasma membrane patches attached to mouse islet β cells exposed to either control vehicle (n=33) or ApoCIII (n=32). (C) Examples of unitary $Ca_v1$ channel currents recorded in plasma membrane patches attached to either a control RINm5F cell or a cell treated with ApoCIII. (D) Average number, open probability, mean closed time and mean open time of unitary $Ca_v1$ channels detected in plasma membrane patches of control RINm5F cells (n=34) or cells incubated with ApoCIII (n=35). *P<0.05 and **P<0.01 versus control.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique, 2nd Ed.* (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides methods identifying candidate compounds for limiting development of and/or treating diabetes, comprising
   (a) contacting a first population of insulin secreting cells with an amount of apolipoprotein CIII (ApoCIII) effective to increase density and/or conductivity of $Ca_v1$ channels, in the presence of one or more test compounds; and
   (b) identifying those positive test compounds that inhibit an ApoCIII-induced increase in density and/or conductivity of $Ca_v1$ channels in the first population of insulin secreting cells compared to control, wherein the positive test compounds are candidate compounds for limiting development of and/or treating diabetes.

The inventors have discovered that ApoCIII incubation caused significant increases in $Ca_v1$ channel open probability and density at single channel levels. The treatment significantly enhanced whole-cell $Ca^{2+}$ currents and the $Ca_v1$ channel blocker nimodipine completely abrogated the enhancement. The inventors have further discovered that coinhibition of PKA and Src kinase was sufficient for the same counteraction, and that knockdown of β1 integrin prevented ApoCIII from hyperactivating β cell $Ca_v$ channels. Thus, the inventors have pinpointed therapeutic targets for limiting $Ca^{2+}$-dependent pancreatic β cell death, and thus for limiting and/or treating diabetes mellitus. Thus, the methods of this aspect of the invention can be used to identify compounds for limiting $Ca^{2+}$-dependent pancreatic β cell death and thus for limiting development of and/or treating diabetes.

As used herein, "apoCIII" refers to a protein comprising the amino acid sequence shown in SEQ ID NO:2 (Human) (NCBI accession number CAA25233), SEQ ID NO:4 (Rat) (NCBI accession number AA40746), or SEQ ID NO:6 (Macaque) (NCBI accession number CAA48419), or functional equivalents thereof.

The apoCIII may be substantially purified apoCIII, available, for example, from Sigma Chemical Company (St. Louis, Mo.), wherein "substantially purified" means that it is removed from its normal in vivo cellular environment. Alternatively, the apoCIII may be present in a mixture, such as blood serum from type 1 diabetic or partially or fully purified therefrom using standard techniques, such as those described below. In a preferred embodiment, substantially purified apoCIII is used.

As discussed below, there are three known isoforms of human apoCIII that have the same amino acid sequence, but which differ in their glycosylation pattern. Thus, in a preferred embodiment, glycosylated apoCIII is used, wherein the glycosylation is preferably sialylation. In another preferred embodiment, mono-sialylated or di-sialylated apoCIII is used. Such glycosylated forms may be purchased, for example, from Sigma Chemical Company, or may be partially or fully purified using standard techniques, such as those described below.

Any suitable insulin secreting cell can be used, including but not limited to pancreatic β cells. As used herein, "pancreatic β cells" are any population of cells that contain pancreatic β islet cells. The cells can be obtained from any mammalian species, or may be present within the mammalian species when the assays are conducted in vivo. Such pancreatic β islet cell populations include the pancreas, isolated pancreatic islets of Langerhans ("pancreatic islets"), isolated pancreatic β islet cells, and insulin secreting cell lines. Methods for pancreatic isolation are well known in the art, and methods for isolating pancreatic islets, can be found, for example, in Cejvan et al., Diabetes 52:1176-1181 (2003); Zambre et al., Biochem. Pharmacol. 57:1159-1164 (1999), and Fagan et al., Surgery 124:254-259 (1998), and references cited therein. Insulin secreting cell lines are available from the American Tissue Culture Collection ("ATCC") (Rockville, Md.). In a further embodiment where pancreatic β cells are used, they are obtained from ob/ob mice, which contain more than 95% β cells in their islets, and are commercially available.

Measuring the density and/or conductivity of $Ca_v1$ channels can be carried out by standard methods in the art, including but not limited to single channel and whole-cell patch-clamp measurements (cell-attached and perforated whole-cell patch-clamp techniques). As used herein, "increase density and/or conductivity of $Ca_v1$ channels" refers to increasing during the course of the assay above that seen in the absence of test compounds. The method does not require a specific amount of increase in density and/or conductivity of $Ca_v1$ channels over baseline, so long as the compound(s) promotes an increase in density and/or conductivity of $Ca_v1$ channels above that seen in the absence of test compounds. In a preferred embodiment, the increase is a statistically significant increase as judged by standard statistical analysis.

The contacting of the pancreatic β cells with the apoCIII may occur before, after, or simultaneously with contacting the cells with one or more test compounds. The contacting can be in vitro or in vivo (ex: in an experimental animal model). Any suitable culture conditions can be used for carrying out the methods of any of the candidate identification methods of the invention. In one embodiment, the cells are contacted with ApoCIII for at least 6 hours. In another embodiment, the cells are grown in medium comprising between 1 mM and 15 mM glucose; preferably between 3 mM and 12 mM; preferably about 11 mM glucose. In a further embodiment, the cells are cultured at approximately 37° C. (preferably in a humidified incubator, such as 5% $CO_2$) prior to recording the density and/or conductivity of the $Ca_v1$ channels at approximately room temperature. These and other suitable assay conditions are well within the level of those of skill in the art, based on the teachings herein.

In one embodiment, the candidate compounds are candidate compounds for limiting development of and/or treating type 1 diabetes. In another embodiment, the candidate compounds are candidate compounds for limiting development of and/or treating type 2 diabetes. The present invention further provides compounds identified by the above screening methods, and their use for treating subjects in need thereof.

In another embodiment, the methods further comprise large-scale synthesis of the test compounds that inhibit apoCIII-induced increase in density and/or conductivity of $Ca_v1$ channels in the pancreatic β cells.

When the test compounds comprise polypeptide sequences, such polypeptides may be chemically synthesized or recombinantly expressed. Recombinant expression can be accomplished using standard methods in the art, as disclosed above. Such expression vectors can comprise bacterial or viral expression vectors, and such host cells can be prokaryotic or eukaryotic. Synthetic polypeptides, prepared using the well-known techniques of solid phase, liquid phase, or peptide condensation techniques, or any combination thereof, can include natural and unnatural amino acids. Amino acids used for peptide synthesis may be standard Boc (Nα-amino protected Nα-t-butyloxycarbonyl) amino acid resin with standard deprotecting, neutralization, coupling and wash protocols, or standard base-labile Nα-amino protected 9-fluorenylmethoxycarbonyl (Fmoc) amino acids. Both Fmoc and Roc No-amino protected amino acids can be obtained from Sigma, Cambridge Research Biochemical, or other chemical companies familiar to those skilled in the art. In addition, the polypeptides can be synthesized with other No-protecting groups that are familiar to those skilled in this art. Solid phase peptide synthesis may be accomplished by techniques familiar to those in the art and provided, such as by using automated synthesizers.

When the test compounds comprise antibodies, such antibodies can be polyclonal or monoclonal. The antibodies can be humanized, fully human, or murine forms of the antibodies. Such antibodies can be made by well-known methods, such as described in Harlow and Lane, Antibodies; A Laboratory Manual, Cold Spring Harbor Laboratory, Cold Spring Harbor, N.Y., (1988).

When the test compounds comprise nucleic acid sequences, such nucleic acids may be chemically synthesized or recombinantly expressed as well. Recombinant expression techniques are well known to those in the art (See, for example, Sambrook, et al., 1989, supra). The nucleic acids may be DNA or RNA, and may be single stranded or double. Similarly, such nucleic acids can be chemically or enzymatically synthesized by manual or automated reactions, using standard techniques in the art. If synthesized chemically or by in vitro enzymatic synthesis, the nucleic acid may be purified prior to introduction into the cell. For example, the nucleic acids can be purified from a mixture by extraction with a solvent or resin, precipitation, electrophoresis, chromatography, or a combination thereof. Alternatively, the nucleic acids may be used with no or a minimum of purification to avoid losses due to sample processing.

When the test compounds comprise compounds other than polypeptides, antibodies, or nucleic acids, such compounds can be made by any of the variety of methods in the art for conducting organic chemical synthesis.

In one embodiment, the control comprises contacting a second population of insulin secreting cells with an amount of apolipoprotein CIII (ApoCIII) effective to increase density and/or conductivity of $Ca_v1$ channels, in the absence of one or more test compounds. This embodiment, which can be combined with the use of any of the other controls disclosed herein, may comprise, for example, contacting the second population of cells with a formulation, such as a buffer, that is similar to or identical to the formulation the test compounds are dissolved in.

In one embodiment, the control comprises contacting a control population of insulin secreting cells with an amount of ApoCIII effective to increase density and/or conductivity of $Ca_v1$ channels, in the presence of the one or more test compounds, and further contacting the control population of insulin secreting cells with $Ca_v2$ and/or $Ca_v3$ channel blockers, including but not limited to ω-agatoxin IVA, ω-conotoxin GVIA and SNX 482 ($Ca_v2$ channel blockers); and mibefradil and NNC 55-0396 ($Ca_v3$ channel blockers), wherein positive test compounds that inhibit the ApoCIII-induced increase in density and/or conductivity of $Ca_v1$ channels in the $Ca_v2$ and/or $Ca_v3$ channel blocker-control population of insulin secreting cells to a greater degree than in the first population of insulin secreting cells are candidate compounds for limiting development of and/or treating diabetes. In this embodiment, the $Ca_v2$ and/or $Ca_v3$ channel blocker are selective for the $Ca_v2$ and/or $Ca_v3$ channel, and do not serve as a $Ca_v1$ channel blocker. It is within the level of those of skill in the art to determine, based on the teachings herein, the amount of any $Ca_v2$ and/or $Ca_v3$ channel blocker(s) that can be usefully used in a given assay.

In another embodiment, the control comprises contacting a control population of insulin secreting cells with an amount of ApoCIII effective to increase density and/or conductivity of $Ca_v1$ channels, in the presence of the one or more test compounds, and further contacting the control population of insulin secreting cells with a Src kinase inhibitor and/or a PKA inhibitor, wherein positive test compounds that inhibit the ApoCIII-induced increase in density and/or conductivity of $Ca_v1$ channels in the first population of insulin secreting cells to a greater degree than in the Src kinase inhibitor and/or a PKA inhibitor control population of insulin secreting cells are candidate compounds for limiting development of and/or treating diabetes. Exemplary Src kinase inhibitors include PP1 analogs, PP2, and compounds disclosed in the examples that follow. Exemplary PKA inhibitors include adenosine 3',5'-cyclic monophosphorothioate-R, H-7, H-8, H-9, H-89, and compounds disclosed in the examples that follow.

As shown in the examples that follow, the inventors have discovered that ApoCIII hyperactivates β cell $Ca_v1$ channels through integrin-dependent co-activation of PKA and Src kinase. Thus, inhibitors of PKA and/or Src should downregulate positive candidate compounds of the present invention. Any suitable PKA and/or Src kinase inhibitor can be used, including but not limited to those disclosed in the examples that follow. It is within the level of those of skill in the art to determine, based on the teachings herein, the amount of any Src kinase inhibitor(s) and/or a PKA inhibitor(s) that can be usefully used in a given assay.

In a further embodiment, the control comprises contacting a control population of insulin secreting cells with an amount of ApoCIII effective to increase density and/or conductivity of $Ca_v1$ channels, in the presence of the one or more test compounds and further contacting the control population of insulin secreting cells with a molecule that inhibits β1 integrin expression or activity, wherein positive test compounds that inhibit the ApoCIII-induced increase in density and/or conductivity of $Ca_v1$ channels in the first population of insulin secreting cells to a greater degree than in the β1 integrin inhibitor control population of insulin secreting cells are candidate compounds for limiting development of and/or treating diabetes. As shown in the examples that follow, the inventors have discovered that ApoCIII hyperactivates β cell $Ca_v1$ channels through β1 integrin-dependent coactivation of PKA and Src kinase. Thus, inhibitors of β1 integrin should down-regulate positive candidate compounds of the present invention. Any suitable β1 integrin inhibitor can be used (antibodies, antisense, siRNA, shRNA, etc.), including but not limited to those disclosed in the examples that follow. It is within the level of those of skill in the art to determine, based on the teachings herein, the amount of any β1 integrin inhibitor(s) that can be usefully used in a given assay.

As will be understood by those of skill in the art, a single control can be used in carrying out the methods of the invention, including but not limited to any of the controls disclosed above. Alternatively, multiple control embodiments can be used (2, 3, or more, including but not limited to any of the controls disclosed above), wherein each embodiment utilizes a different control cell population.

In a second aspect, the present invention provides methods for identifying candidate compounds for limiting development of and/or treating diabetes, comprising
  (a) contacting a first population of insulin secreting cells with an amount of ApoCIII effective to increase density and/or conductivity of $Ca_v1$ channels, in the presence of one or more test compounds; and
  (b) identifying those positive test compounds that inhibit β1 integrin expression or activity in the first population of insulin secreting cells compared to control, wherein the positive test compounds are candidate compounds for limiting development of and/or treating diabetes.

In one embodiment, the control comprises contacting a second population of insulin secreting cells contacted with an amount of ApoCIII effective to increase density and/or conductivity of $Ca_v1$ channels, in the absence of one or more test compounds. This embodiment may comprise, for example, contacting the second population of cells with a formulation, such as a buffer, that is similar to or identical to the formulation the test compounds are dissolved in.

All embodiments of the first aspect of the invention can be used in this second aspect unless the context clearly dictates otherwise.

In one embodiment, the control comprises contacting a second population of insulin secreting cells contacted with ApoCIII in the absence of test compounds. This embodiment may comprise, for example, contacting the second population of cells with a formulation, such as a buffer, that is similar to or identical to the formulation the test compounds are dissolved in.

In a third aspect, the present invention provides methods for identifying candidate compounds for limiting development of and/or treating diabetes, comprising
  (a) contacting a first population of insulin secreting cells with an amount of ApoCIII effective to increase density and/or conductivity of $Ca_v1$ channels, in the presence of one or more test compounds; and
  (b) identifying those positive test compounds that inhibit activation of PKA and/or Src kinase in the first population of insulin secreting cells compared to control, wherein the positive test compounds are candidate compounds for limiting development of and/or treating diabetes.

In one embodiment, the methods comprise identifying inhibitors of β1 integrin-mediated activation of PKA and/or Src kinase.

In one embodiment, the control comprises contacting a second population of insulin secreting cells contacted with an amount of ApoCIII effective to increase density and/or conductivity of $Ca_v1$ channels, in the absence of one or more test compounds. This embodiment may comprise, for example, contacting the second population of cells with a formulation, such as a buffer, that is similar to or identical to the formulation the test compounds are dissolved in.

All embodiments of the first aspect of the invention can be used in this third aspect unless the context clearly dictates otherwise.

In a further aspect, the present invention provides methods for treating or limiting development of diabetes, comprising administering to a subject in need thereof an amount effective of an inhibitor of PKA and Src kinase to treat or limit development of diabetes. Exemplary Src kinase inhibitors include PP1 analogs, PP2, and compounds disclosed in the examples that follow. Exemplary PKA inhibitors include adenosine 3',5'-cyclic monophosphorothioate-R, H-7, H-8, H-9, H-89, and compounds disclosed in the examples that follow.

In another aspect, the present invention provides methods for treating or limiting development of diabetes, comprising administering to a subject in need thereof with an amount effective of an inhibitor of β1 integrin expression and/or activity. In various embodiments, the inhibitor is selected from the group consisting of an anti-β1 integrin antibody, anti-β1 integrin aptamer, β1 integrin siRNA, β1 integrin shRNA, and β1 integrin antisense oligonucleotides.

In a still further aspect, the present invention provides methods for treating or limiting development of diabetes, comprising administering to a subject in need thereof with an amount effective of an inhibitor of ApoCIII activation of pancreatic β cells.

As used herein, an "inhibitor" of apoCIII activation includes compounds that reduce the transcription of apoCIII DNA into RNA, compounds that reduce translation of the apoCIII RNA into protein, and compounds that reduce the function of apoCIII protein. Such inhibiting can be complete inhibition or partial inhibition, such that the expression and/or activity of the apoCIII is reduced, resulting in a reduced ability to increase intracellular calcium concentration. Such inhibitors are selected from the group consisting of antibodies that bind to apoCIII; aptamers that can interfere with apoCIII activity; antisense oligonucleotides directed against the apoCIII protein, DNA, or mRNA; small interfering RNAs (siRNAs) or short hairpin RNAs (shRNAs) directed against the apoCIII protein, DNA, or mRNA, and any other chemical or biological compound that can interfere with apoCIII activity.

In one embodiment of each of these therapeutic aspects, the method is for treating diabetes. In this embodiment, the subject has been diagnosed with type 1 or type 2 diabetes. As used herein, "diabetes" is characterized by insufficient or no production of insulin by the pancreas, leading to high blood sugar levels.

As used herein, "treating diabetes" means accomplishing one or more of the following: (a) reducing the severity of the diabetes or diabetic complications; (b) limiting or preventing development of diabetic complications; (c) inhibiting worsening of diabetic complications or of symptoms characteristic of diabetes; (d) limiting or preventing recurrence diabetic complications or of symptoms characteristic of diabetes; (e) limiting or preventing recurrence of diabetic complications or of symptoms characteristic of diabetes in patients that were previously symptomatic.

Symptoms characteristic of diabetes include, but are not limited to, elevated blood glucose levels, decreased insulin production, insulin resistance, proteinuria, and impaired glomerular clearance. Diabetic complications that can be treated according to the methods of the invention include, but are not limited to, complications in the nerves (such as diabetic neuropathy) and complications associated with smooth muscle cell dysregulaton (including but not limited to erectile dysfunction, bladder dysfunction, and vascular complications including but not limited to atherosclerosis, stroke, and peripheral vascular disease)

In another embodiment, the method is for limiting development of diabetes. In this aspect, the subject is at risk of type 1 or type 2 diabetes, and a benefit is to limit development of diabetes and/or diabetic complications. Any subject at risk of developing diabetes can be treated, including but not limited to subjects with one or more of, metabolic syndrome, known genetic risk factors for diabetes, a family history of diabetes, and obesity.

In a further embodiment, the methods for treating or limiting development of diabetes and/or diabetic complications further comprises treating those individuals that have been identified as overexpressing apoCIII compared to control. Increases in apoCIII expression precede development of diabetic complications, and thus this embodiment permits early detection of suitable patients for treatment using the methods of the invention.

As used herein, "overexpression" is any amount of apoCIII expression above control. Any suitable control can be used, including apoCIII expression levels from a subject known not to be suffering from diabetes, or previously determined standardized expression levels of apoCIII from a population of similar patient samples. Any amount of increased apoCIII expression relative to control is considered "overexpression"; in various embodiments, the overexpression comprises at least 10%, 20%, 50%, 100%, 200%, or greater increased apoCIII expression compared to control. In a preferred embodiment, apoCIII expression is detected in blood or serum samples. In one embodiment to evaluate the levels of apoCIII in pos, neg, and control sera, albumin is removed from serum samples using standard techniques, such as via use of Montage Albumin Deplete Kit (Millipore) or AlbuSorb™ (Biotech Support Group). The collected sera samples can then be freeze-dried overnight and run on sep-Pak C18. The eluted proteins can be freeze-dried and thereafter dissolved in 100 µL 0.1% TFA and run on an ACE C18 10–×0.21-cm column 20-60%, and the area under the curve, where apoCIII elutes, evaluated. ApoCIII can be identified using any suitable technique, including but not limited to MALDI mass spectrometry.

As used herein, the term "subject" or "patient" is meant any subject for which therapy is desired, including humans, cattle, dogs, cats, guinea pigs, rabbits, rats, mice, insects, horses, chickens, and so on. Most preferably, the subject is human.

The therapeutic may be administered by any suitable route, including but not limited to oral, topical, parenteral, intranasal, pulmonary, or rectal in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of the invention and a pharmaceutically acceptable carrier The therapeutic may be present in association with one or more non-toxic pharmaceutically acceptable carriers and/or diluents and/or adjuvants, and if desired other active ingredients. The therapeutic may be in a form suitable for oral use, for example, as tablets, troches, lozenges, aqueous or oily suspensions, dispersible powders or granules, emulsion, hard or soft capsules, or syrups or elixirs.

The dosage range depends on the choice of the compound, the route of administration, the nature of the formulation, the nature of the subject's condition, and the judgment of the attending practitioner. For example, oral administration would be expected to require higher dosages than administration by intravenous injection. Variations in these dosage levels can be adjusted using standard empirical routines for optimization, as is well understood in the art Example 1. Apolipoprotein CIII Hyperactivates β Cell $Ca_V1$ Channels Through β1 Integrin-Dependent Coactivation of PKA and Src Kinase

SUMMARY

Apolipoprotein CIII (ApoCII) not only serves as an inhibitor of triglyceride hydrolysis, but also participates in diabetes-related pathological events such as the inflammatory process and hyperactivation of voltage-gated $Ca^{2+}$ ($Ca_V$) channels in the pancreatic β cell. However, nothing is known about the molecular mechanisms whereby ApoCIII hyperactivates β cell $Ca_V$ channels. We now demonstrate that ApoCIII increased $Ca_V1$ channel open probability and density. ApoCIII enhanced whole-cell $Ca^{2+}$ currents and the $Ca_V1$ channel blocker nimodipine completely abrogated this enhancement. The effect of ApoCIII was not significantly influenced by individual inhibition of PKA, PKC or Src kinase. However, combined inhibition of PKA, PKC and Src kinase counteracted the effect of ApoCIII, similar results obtained by coinhibition of PKA and Src kinase. Moreover, knockdown of β1 integrin prevented ApoCIII from hyperactivating β cell $Ca_V$ channels. These data reveal that ApoCIII hyperactivates β cell $Ca_V1$ channels through β1 integrin-dependent coactivation of PKA and Src kinase.

Introduction

Voltage-gated calcium ($Ca_V$) channels are critical in pancreatic β cell physiology and pathophysiology (Yang and Berggren, 2005; Yang and Berggren, 2006). They not only take center stage in the regulation of insulin secretion, but are also involved in β cell development, survival and growth through the regulation of protein phosphorylation, gene expression and the cell cycle (Yang and Berggren, 2005; Yang and Berggren, 2006). The function and density of β cell $Ca_V$ channels are regulated by a wide range of mechanisms either shared by other cell types or specific to β cells, e.g., channel phosphorylation, interaction with other molecules and glucose metabolism-derived signaling (Catterall, 2000; Yang and Berggren, 2005; Yang and Berggren, 2006). Dysfunctional $Ca_V$ channels cause β cell malfunction and even death as manifested in the most common metabolic disorder diabetes mellitus (Yang and Berggren, 2005; Yang and Berggren, 2006). Indeed, a T-lymphocyte-mediated autoimmune attack plays a crucial role in β cell death in type 1 diabetes. In addition, factors in type 1 diabetic serum compel unphysiological amounts of $Ca^{2+}$ to enter pancreatic β cells through hyperactivation of β cell $Ca_V$ channels resulting in β cell apoptosis. Undoubtedly, this process aggravates the disease development on top of the autoimmune attack (Yang and Berggren, 2005; Yang and Berggren, 2006). Such factors are also visualized in type 2 diabetic serum where they behave in the same way as they do in type 1 diabetic serum (Juntti-Berggren et al., 1993; Juntti-Berggren et al., 2004; Sol et al., 2009). In fact, reduction in β cell mass and hyperactivation of β cell $Ca_V$ channels appear under the type 2 diabetic conditions such as those in the Goto-Kakizaki rat (Kato et al., 1996).

It has been demonstrated that elevated apolipoprotein CIII (ApoCIII) acts as a diabetologenic serum factor to drive β cell destruction via hyperactivation of β cell $Ca_V$ channels (Juntti-Berggren et al., 2004; Sol et al., 2009). Moreover, we have recently shown that in vivo suppression of ApoCIII delays onset of diabetes in the BioBreeding rat, a rat model for human type 1 diabetes (Holmberg et al., 2011). Normally, ApoCIII is a blood plasma component. It is synthesized predominantly in the liver and to a minor extent in the intestine. Liver and intestinal cells release this apolipoprotein into the blood where it is situated on the surface of chylomicrons, very low density lipoproteins (LDLs) and high density lipoproteins (HDLs) (Gangabadage et al., 2008; Jong et al., 1999). ApoCIII is composed of 79 amino acid residues that form six amphiphilic α-helixes, each containing about 10 residues. The three-dimensional NMR structure and dynamics of ApoCIII have been resolved when it complexes with sodium dodecyl sulfate micelles, mimicking its natural lipid-bound state. The six amphiphilic α-helixes assemble into a necklace-like chain wrapping around the sodium dodecyl sulfate micelle surface (Gangabadage et al., 2008). Dogmatically, ApoCIII serves as an effective inhibitor of triglyceride hydrolysis by inhibiting lipoprotein lipase and through interference with triglyceride-rich lipoproteins binding to the negatively charged cell surface where lipoprotein lipases and lipoprotein receptors reside (Gangabadage et al., 2008; Jong et al., 1999). It impedes the selective uptake of cholesteryl esters from LDL and HDL by binding to the scavenger receptor class B type 1 (SR-BI), and hampers the endocytosis of cholesterol-rich LDL by prevention of apolipoprotein B binding to LDL receptors (Clavey et al., 1995; Huard et al., 2005; Xu et al., 1997). Elevated plasma ApoCIII concentration is a feature of dyslipidemia in obesity and observed in both type 1 and type 2 diabetes (Chan et al., 2002; Juntti-Berggren et al., 2004; Sundsten et al., 2008), whereas a group of Ashkennazi Jewish with reduced plasma ApoCIII concentration maintains cardiovascular health and greater insulin sensitivity with age and reaches exceptional longevity (Atzmon et al., 2006).

In addition to the dogmatic roles in lipid metabolism, ApoCII is also a multifaceted player in cell signaling. It can bind to distinct cell surface receptors including scavenger receptor class B type I (SR-BI), Toll-like receptor 2 (TLR2) and uncharacterized binding sites relaying corresponding signals to their downstream effectors, e.g., β1 integrin, pertussis toxin-sensitive G proteins, NF-κB and protein kinases (Fang and Liu, 2000; Kawakami et al., 2006; Kawakami et al., 2007; Xu et al., 1997). However, nothing is known about the molecular mechanisms whereby ApoCIII hyperactivates β cell $Ca_V$ channels. In the present study, we demonstrate that ApoCIII upregulates β cell $Ca_V1$ channels through β1 integrin-dependent coactivation of PKA and Src kinase.

Results

Apolipoprotein CIII Increases $Ca_V1$ Channel Density and Conductivity in the β Cell Our previous work reveals that ApoCIII incubation significantly enhances whole-cell $Ca^{2+}$ currents in the mouse islet (cell (Juntti-Berggren et al., 2004). To clarify what type of β cell $Ca_V$ channels and whether the density or conductivity was affected, we analyzed unitary $Ca_V1$ channel currents, characterized by a large unitary $Ba^{2+}$ conductance with long-lasting openings, in mouse islet β cells (FIG. 1A) and RINm5F cells (FIG. 1C) following ApoCIII incubation. In experiments with mouse islet β cells, we observed more $Ca_V1$ channels, reflected by more layers of unitary $Ba^{2+}$ currents, in plasma membrane patches of ApoCIII-treated cells than in those of control cells (FIG. 1A). The average number, open probability and mean open time of unitary $Ca_V1$ channels in ApoCIII-treated cells (n=32) were significantly greater than those in cells exposed to control vehicle (n=33) (FIG. 1B). The mean closed time of unitary $Ca_V1$ channels recorded in patches of ApoCIII-incubated cells was significantly shorter than that in control patches (FIG. 1B). Likewise, similar effects of ApoCIII occurred on $Ca_V1$ channels in insulin-secreting RINm5F cells. Plasma membrane patches of ApoCIII-incubated cells accommodated more $Ca_V1$ channels in comparison with those of vehicle-treated cells (FIG. 1C). $Ca_V1$ channels in the former opened more frequently than those in the latter (FIG. 1C). ApoCIII incubation (n=35) significantly increased channel number, elevated open probability, prolonged mean open time and shortened mean closed time of $Ca_V1$ channels as compared with incubation with vehicle solution (n=34) (FIG. 1D). Obviously, the data reveal that ApoCIII increased both density and conductivity of β cell $Ca_V1$ channels.

Figure 2:
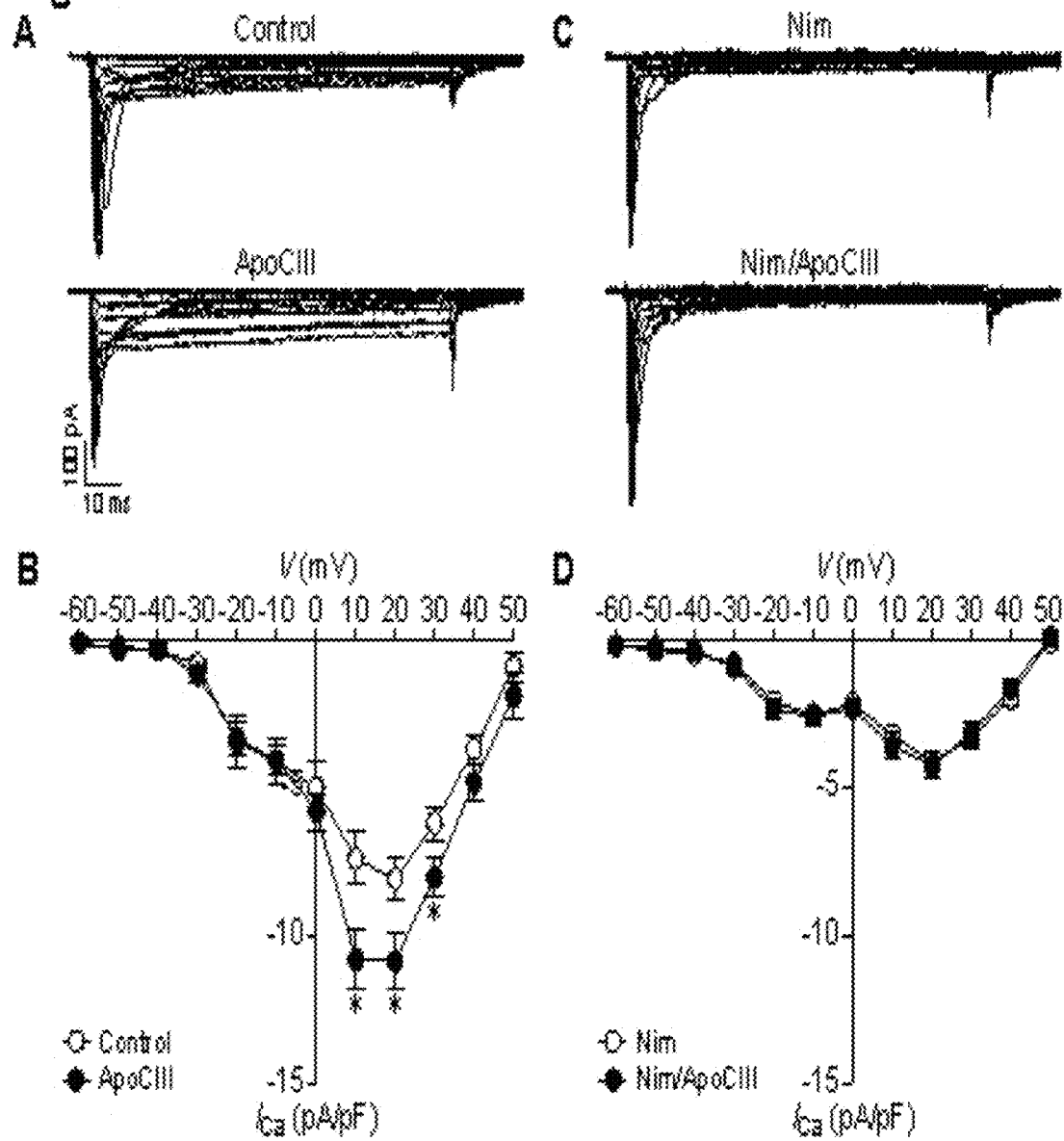
FIG. 2. Apolipoprotein CIII incubation increases whole-cell $Ca^{2+}$ currents and coincubation with the $Ca_v1$ channel blocker nimodipine abrogates the effect of apolipoprotein CIII incubation in RINm5F cells. (A) Sample whole-cell $Ca^{2+}$ current traces from a cell incubated with vehicle solution as control (cell capacitance: 10.1 pF) and apolipoprotein CIII (ApoCIII)-treated cell (cell capacitance: 11.1 pF). (B) Average $Ca^{2+}$ current density-voltage relationships in control cells (open circles, n=26) and cells treated with ApoCIII (filled circles, n=26). *P<0.05 and **P<0.01 versus control. (C) Sample whole-cell $Ca^{2+}$ current traces from a nimodipine (Nim)-incubated cell (cell capacitance: 10 pF) and a cell exposed to Nim together with ApoCIII (Nim/ApoCIII) (cell capacitance: 11.9 pF). (D) Average $Ca^{2+}$ current density-voltage relationships in Nim-treated cells (open circles, n=20) and cells incubated with Nim/ApoCIII (filled circles, n=21). *P<0.05 and **P<0.01 versus Nim alone.

Pharmacological Ablation of $Ca_V1$ Channels Prevents Apolipoprotein CIII-Induced Hyperactivation of β Cell $Ca_V$ Channels The verification of the effects of ApoCIII on $Ca_V1$ channels by single channel analysis does not necessarily mean that ApoCIII only attacks $Ca_V1$ channels. To examine if the effects also occur on other types of $Ca_V$ channels, we analyzed whole-cell $Ca^{2+}$ currents in RINm5F cells following ApoCIII incubation in the absence and presence of the $Ca_V1$ channel blocker nimodipine. Whole-cell $Ca^{2+}$ currents in cells incubated with ApoCIII were larger than those in cells treated with vehicle solution (FIG. 2A). Whole-cell $Ca^{2+}$ current densities observed in the voltage range from 10 to 30 mV in the ApoCIII group were significantly higher than those in the control group (FIG. 2B). In striking contrast, whole-cell $Ca^{2+}$ currents were similar between control cells and cells incubated with ApoCIII in the presence of nimodipine (FIG. 2C). There was no significant difference in the whole-cell $Ca^{2+}$ current density between the two treatments (FIG. 2D). The data confirm that ApoCIII solely impinge on β cell $Ca_V1$ channels.

Apolipoprotein CIII Hyperactivates β Cell $Ca_V$ Channels Via Coactivation of PKA and Src Kinase The increase in open probability of β cell $Ca_V1$ channels by ApoCIII and the mediating role of protein kinases in ApoCIII signaling suggest that ApoCIII may signal upstream of some protein kinases to hyperactivate β cell $Ca_V1$ channels (Gui et al., 2006; Kawakami et al., 2006; Rueckschloss and Isenberg, 2004; Waitkus-Edwards et al., 2002; Wu et al., 2001). Therefore, we explored the involvement of PKA, PKC and Src kinase in ApoCIII-induced hyperactivation of β cell $Ca_V$ channels.

Figure 3:
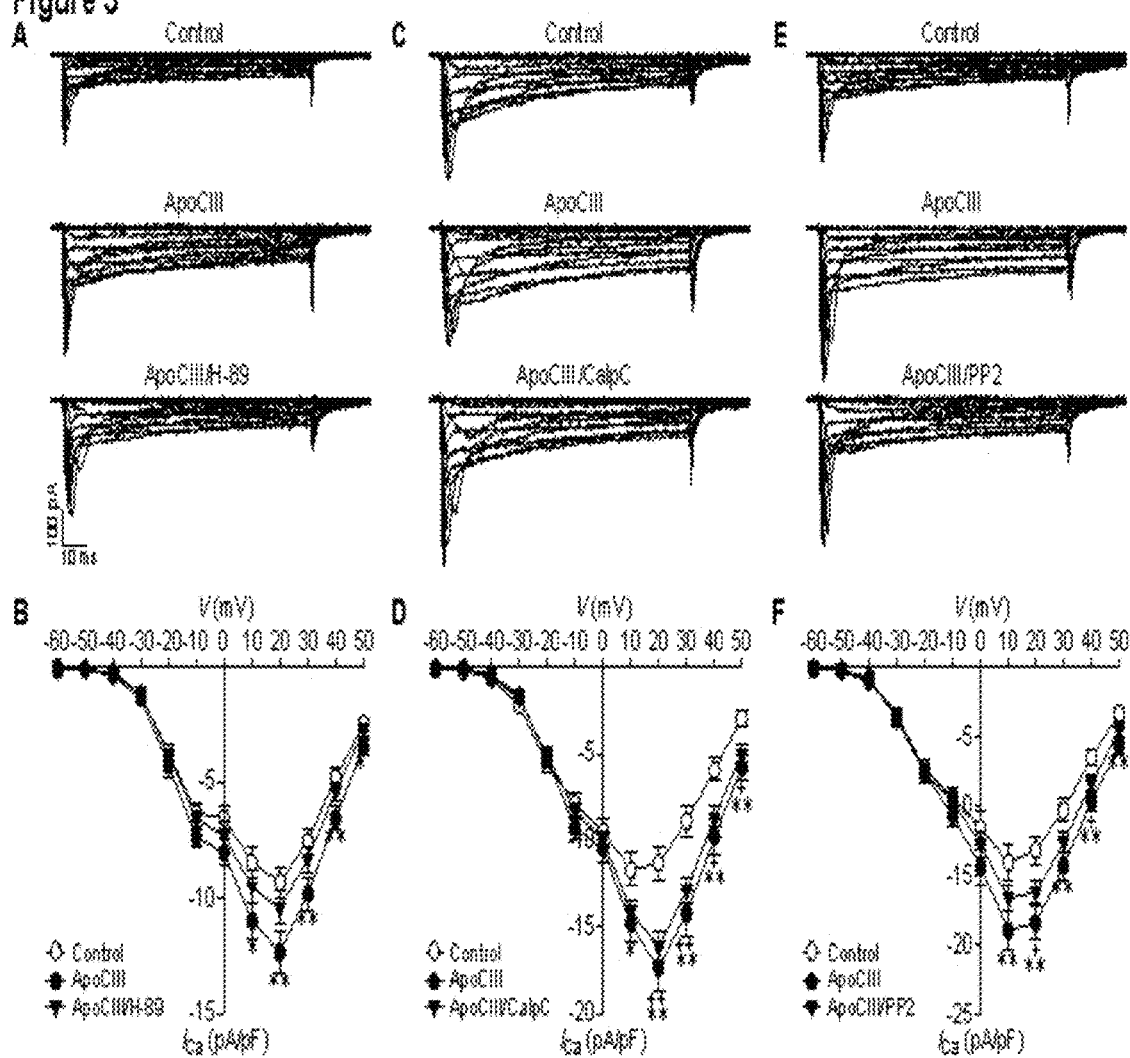
FIG. 3. PKA or Src kinase inhibition marginally reduces, but PKC inhibition does not affect apolipoprotein CIII-induced enhancement of whole-cell $Ca^{2+}$ currents in RINm5F cells. (A) Sample whole-cell $Ca^{2+}$ current traces from a cell incubated with vehicle solution as control (cell capacitance: 8.5 pF), an apolipoprotein CIII (ApoCIII)-treated cell (cell capacitance: 8.2 pF) and a cell exposed to ApoCIII plus the PKA inhibitor H-89 (ApoCIII/H-89, cell capacitance: 8.4 pF). (B) Average $Ca^{2+}$ current density-voltage relationships in control cells (open circles, n=37) and cells treated with ApoCIII (filled circles, n=36) or ApoCIII/H-89 (filled triangles, n=36). *P<0.05 and **P<0.01 versus control. (C) Sample whole-cell $Ca^{2+}$ current traces registered in a control cell (cell capacitance: 12.5 pF), an ApoCIII-incubated cell (cell capacitance: 12.0 pF) and a cell subjected to cotreatment with ApoCIII and the PKC inhibitor calphostin C (ApoCIII/CalpC, cell capacitance: 12.1 pF). (D) Average $Ca^2$ current density-voltage relationships in control cells (open circles, n=33), ApoCIII-treated cells (filled circles, n=33) and cells exposed to ApoCIII/CalpC (filled triangles, n=33). *P<0.05 and P<0.01 ApoCII versus control. $^+$P<0.05 and $^{++}$P<0.01 ApoCIII/CalpC versus control. (E) Sample whole-cell $Ca^{2+}$ current traces acquired in a control cell (cell capacitance: 9.5 pF), an ApoCIII-incubated cell (cell capacitance: 9.2 pF) and a cell exposed to ApoCIII together with the Src kinase inhibitor PP2 (ApoCIII/PP2, cell capacitance: 10.0 pF). (F) Average $Ca^{2+}$ current density-voltage relationships in control cells (open circles, n=40) and cells incubated with ApoCIII (filled circles, n=40) or ApoCII/PP2 (filled triangles, n=40). P<0.01 ApoCIII versus control. $^+$P<0.05 ApoCIII/PP2 versus control.
Figure 7:
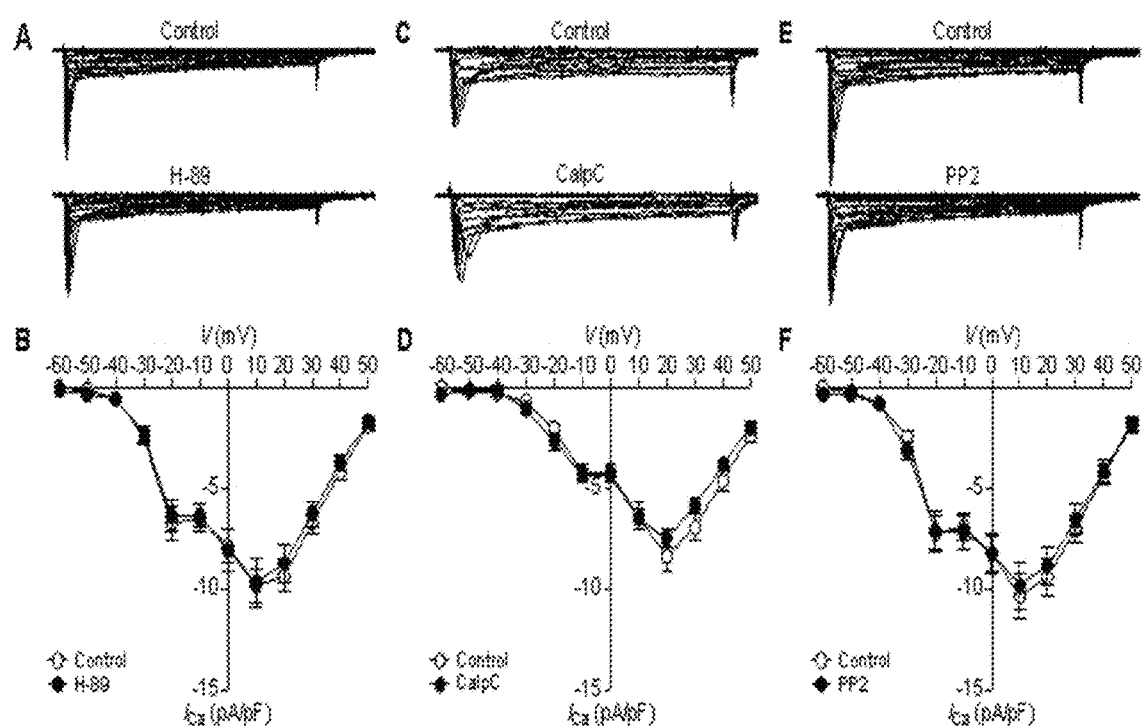
FIG. 7. PKA, PKC or Src kinase inhibition does not alter whole-cell $Ca^{2+}$ currents in RINm5F cells under basal conditions. (A) Sample whole-cell $Ca^{2+}$ current traces from a vehicle-treated cell as control (cell capacitance: 8.8 pF) and a cell exposed to H-89 (cell capacitance: 8.5 pF). (B) Average $Ca^{2+}$ current density-voltage relationships in control cells (open circles; n=20) and cells incubated with H-89 (filled circles, n=20). (C) Sample whole-cell $Ca^{2+}$ current traces recorded in a control cell (cell capacitance: 10.4 pF) and a cell subjected to calphostin C incubation (CalpC, cell capacitance: 11.0 pF). (D) Average $Ca^{2+}$ current density-voltage relationships in control cells (open circles; n=29) and cells exposed to CalpC (filled circles, n=29). (E) Sample whole-cell $Ca^{2+}$ current traces obtained in a control cell (cell capacitance: 9.0 pF) and a PP2-treated cell (cell capacitance: 9.1 pF). (F) Average $Ca^{2+}$ current density-voltage relationships in control cells (open circles, n=20) and cells incubated with PP2 (filled circles, n=19).

First, we examined the effect of the PKA inhibitor H-89 on ApoCIII-induced hyperactivation of β cell $Ca_V$ channels in RINm5F cells. Whole-cell $Ca^{2+}$ currents registered in control cells were larger than those in cells treated with ApoCIII, whereas whole-cell $Ca^{2+}$ currents recorded in cells incubated with ApoCIII plus H-89 sized in between (FIG. 3A). Average $Ca^{2+}$ current densities measured in ApoCIII-treated cells (filled circles, n=36) were significantly higher than those in vehicle control cells (open circles, n=37) at voltages ranging from 10 to 50 mV (FIG. 3B). However, cells following cotreatment of ApoCIII and H-89 (filled triangles, n=36) did not significantly differ from either cells treated with ApoCIII or control cells in terms of $Ca^{2+}$ current density (FIG. 3B). Moreover, H-89 treatment did not significantly influence $Ca^{2+}$ current densities under basal conditions, i.e. in the absence of ApoCIII (FIGS. 7A and B). The results indicate that PKA inhibition marginally reduced ApoCIII-induced hyperactivation of β cell $Ca_V$ channels.

Second, we tested the effect of the PKC inhibitor calphostin C (CalpC) on ApoCIII-induced hyperactivation of β cell $Ca_V$ channels in RINm5F cells. We observed that cells incubated with ApoCIII and ApoCIII/CalpC-cotreated cells displayed similar whole-cell $Ca^{2+}$ currents, which were larger than those acquired in vehicle-treated cells (FIG. 3C). Mean $Ca^{2+}$ current densities in ApoCIII-treated cells (filled circles, n=33) at the voltage range 10-50 mV and cells exposed to ApoCIII/CalpC (filled triangles, n=33) at a voltage range from 20 to 50 mV increased significantly in comparison with vehicle control cells (open circles, n=33) (FIG. 3D). There is no difference between ApoCIII-treated cells and ApoCII/CalpC-cotreated cells with regard to the $Ca^{2+}$ current density (FIG. 3D). Furthermore, cells exposed to control vehicle were similar to a CalpC-treated cells in terms of $Ca^{2+}$ current density (FIGS. 7C and D). The data demonstrate that PKC inhibition does not affect ApoCIII-induced hyperactivation of β cell $Ca_V$ channels.

Third, we evaluated the effect of the Src kinase inhibitor PP2 on ApoCIII-induced hyperactivation of β cell $Ca_V$ channels in RINm5F cells. We found smaller and larger whole-cell $Ca^{2+}$ currents in cells following incubation with vehicle solution and ApoCIII-incubated cells, respectively (FIG. 3E). Cells exposed to ApoCIII and PP2 fell between vehicle control cells and cells treated with ApoCIII with regard to whole-cell $Ca^{2+}$ currents (FIG. 3E). Whole-cell $Ca^{2+}$ current densities quantified in cells treated with ApoCIII (filled circles, n=40) at the voltage range 10-50 mV were significantly elevated as compared with those determined in vehicle control cells (open circles, n=40) (FIG. 3F). Cells subjected to cotreatment of ApoCIII and PP2 (filled triangles, n=40) showed significantly larger $Ca^{2+}$ currents at the voltage range 20-40 mV than vehicle control cells (open circles, n=40). However, the difference in the $Ca^{2+}$ current density between ApoCIII/PP2-cotreated cells and cells incubated with vehicle solution is less prominent than that between cells treated with ApoCIII and vehicle control cells (FIG. 3F). Moreover, vehicle-treated cells (open circles, n=20) and cells incubated with PP2 (filled circles, n=19) exhited similar $Ca^{2+}$ current densities (FIGS. 7E and F). The results suggest that Src kinase inhibition has a tendency to decrease ApoCIII-induced hyperactivation of β cell $Ca_V$ channels.

Figure 4:
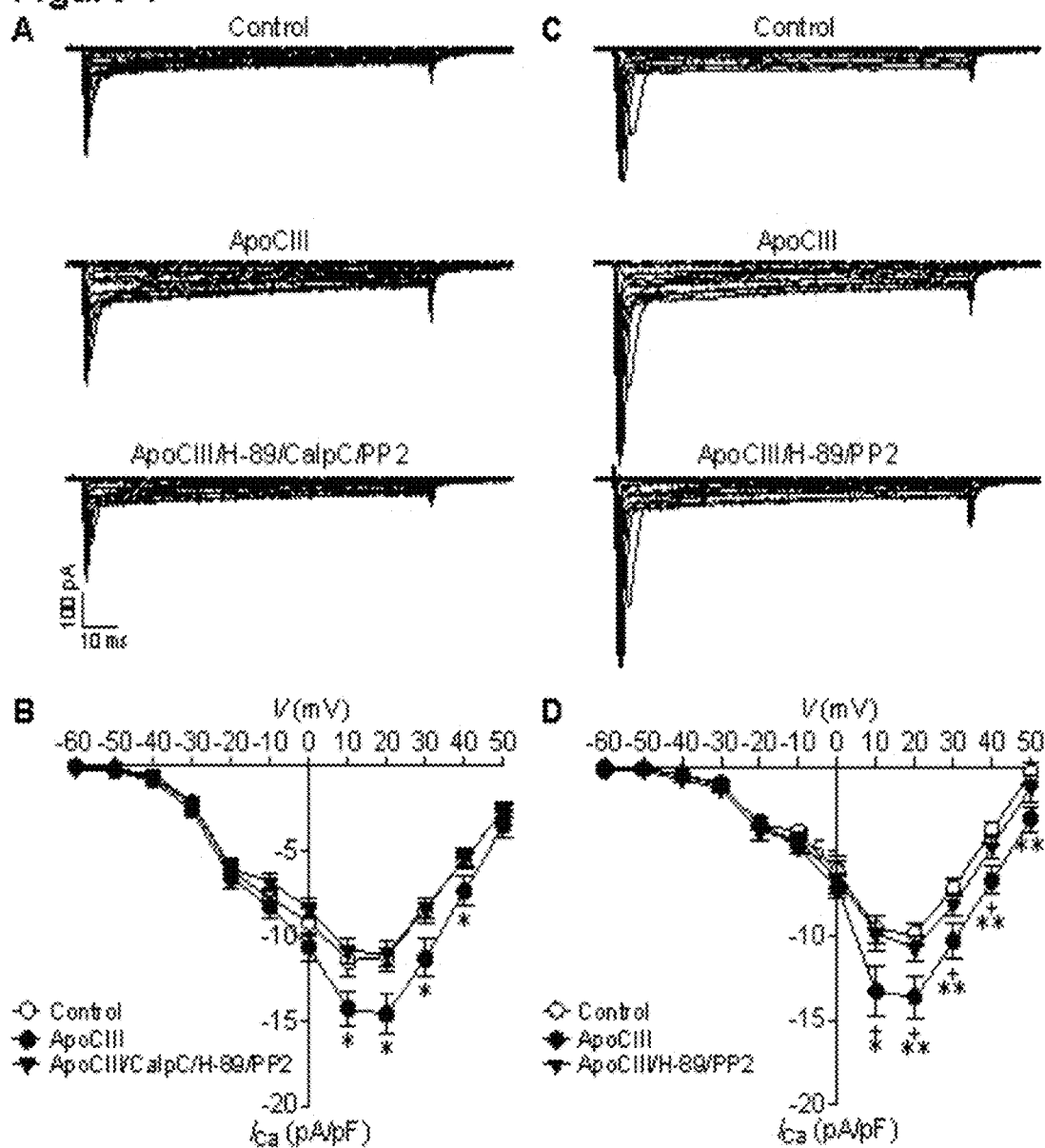
FIG. 4. Combined inhibition of PKA, PKC and Src kinase counteracts apolipoprotein CIII-induced augmentation of whole-cell $Ca^{2+}$ currents in RINm5F cells and coinhibition of PKA and Src kinase is sufficient to obtain this counteraction. (A) Sample whole-cell $Ca^{2+}$ current traces registered in a vehicle-incubated cell (Control, cell capacitance: 7.9 pF), a cell subsequent to apolipoprotein (ApoCIII) treatment (cell capacitance: 7.0 pF) and a cell exposed to ApoCIII in the presence of the protein kinase inhibitor cocktail of H-89, calphostin C and PP2 (ApoCIII/H-89/CalpC/PP2, cell capacitance: 7.2 pF). (B) Average $Ca^{2+}$ current density-voltage relationships in control cells (n=35) and cells exposed to ApoCIII (n=34) or to ApoCIII/H-89/CalpC/PP2 (n=35). *P<0.05 versus control and apoCIII/H-89/CalpC/PP2. (C) Sample whole-cell $Ca^{2+}$ current traces from a control cell (cell capacitance: 8.5 pF), a cell subsequent to ApoCIII treatment (cell capacitance: 8.2 pF) and a cell exposed to ApoCIII in the presence of the protein kinase inhibitors H-89 and PP2 (ApoCIII/H-89/PP2, cell capacitance: 8.7 pF). (D) Average $Ca^2$ current density-voltage relationships in control cells (n=26) and cells subjected to ApoCIII (n=26) or to ApoCIII/H-89/PP2 (n=27). *P<0.05 and **P<0.01 versus control; $^+$P<0.05 versus ApoCIII/H-89/PP2.
Figure 8:
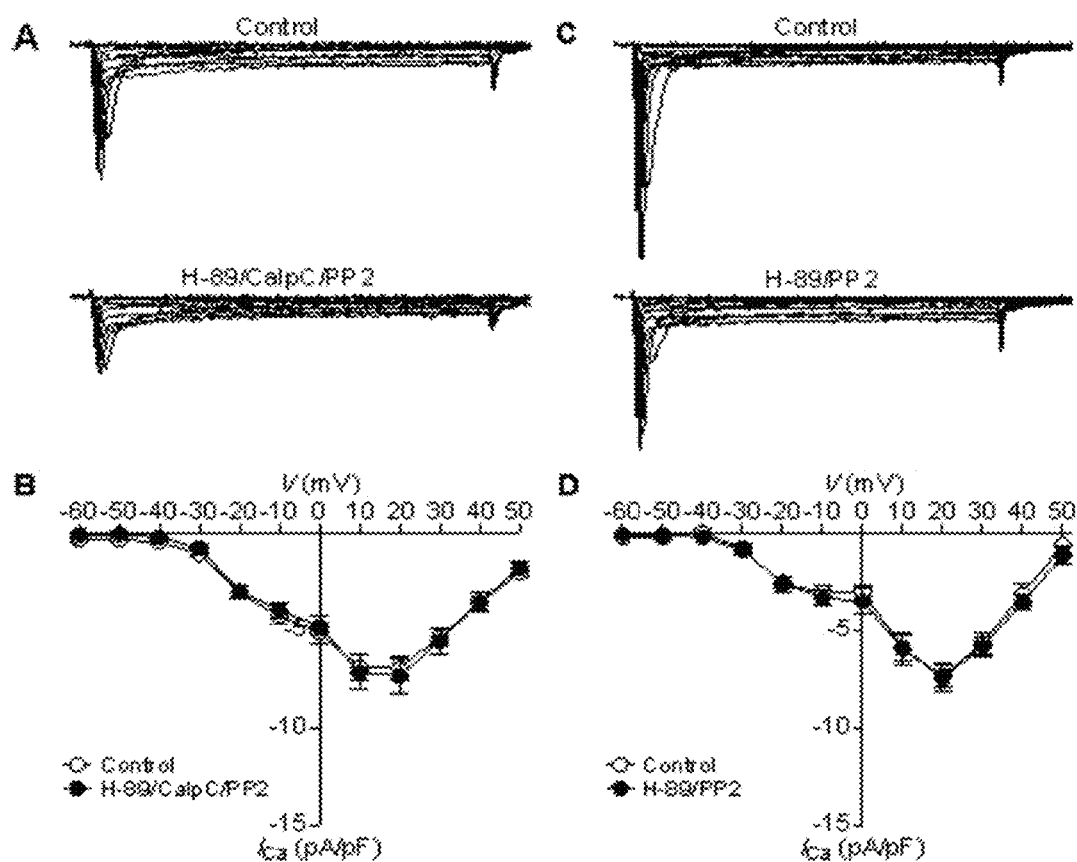
FIG. 8. Combined inhibition of PKA, PKC and Src kinase or coinhibition of PKA and Src kinase does not influence whole-cell $Ca^{2+}$ currents in RINm5F cells under basal conditions. (A) Sample whole-cell $Ca^{2+}$ current traces obtained in a cell incubated with vehicle solution as control (cell capacitance: 10.8 pF) and a cell treated with the protein kinase inhibitor cocktail composed of H-89, calphostin C and PP2 (H-89/CalpC/PP2, cell capacitance: 9.7 pF). (B) Average $Ca^{2+}$ current density-voltage relationships in control cells (open circles, n=30) and cells treated with H-89/CalpC/PP2 (filled circles, n=30). (C) Sample whole-cell $Ca^{2+}$ current traces obtained in a vehicle-treated cell as control (cell capacitance: 9.4 pF) and a cell treated with the protein kinase inhibitors H-89 and PP2 (H-89/PP2, cell capacitance: 9.1 pF). (D) Average $Ca^{2+}$ current density-voltage relationships in control cells (open circles, n=24) and cells treated with H-89/PP2 (filled circles, n=24).

The marginal and null effects of PKA, PKC or Src kinase inhibitors on ApoCIII-induced hyperactivation of β cell $Ca_V$ channels made us wonder what happens if a more complex inhibition of all these kinases is applied. To address this question, we characterized the effect of the protein kinase inhibitor cocktail H-89, CalpC and PP2 on ApoCIII-induced hyperactivation of β cell $Ca_V$ channels in RINm5F cells. Larger whole-cell $Ca^{2+}$ currents appeared in an ApoCIII-treated cells, whereas smaller whole-cell $Ca^{2+}$ currents occurred in vehicle control cells and cells treated with ApoCIII in the presence of H-89, CalpC and PP2 (FIG. 4A). ApoCIII treatment (filled circles, n=35) significantly increased $Ca^{2+}$ current densities at the voltage range 10-50 mV as compared with vehicle control (open circles, n=35) and treatment with ApoCIII together with H-89, CalpC and PP2 (filled triangles, n=34). The profile of $Ca^{2+}$ current densities in cells exposed to ApoCIII in the presence of H-89, CalpC and PP2 resembled that in vehicle control cells (FIG. 4B). Furthermore, treatment of control cells with the protein kinase inhibitor cocktail H-89, CalpC and PP2 had no significant effect on whole-cell $Ca^2$ currents under basal conditions, i.e. in the absence of ApoCIII (FIGS. 8A and B). The results demonstrate that combined inhibition of PKA, PKC and Src kinase effectively ablates ApoCIII-induced hyperactivation of β cell $Ca_V$ channels.

The marginal effect of PKA or Src kinase inhibitors alone on whole-cell $Ca^{2+}$ currents inevitably raised the question if coinhibition of PKA and Src kinase is sufficient to prevent ApoCIII-induced hyperactivation of β cell $Ca_V$ channels. We answered the question by analyzing whole-cell $Ca^{2+}$ currents in RINm5F cells following cotreatment of H-89 and PP2. We observed that whole-cell $Ca^{2+}$ currents in ApoCIII-treated cells were larger than those in control cells or cells subjected to treatment of ApoCIII in the presence of H-89 and PP2 (FIG. 4C). Significantly higher densities of whole-cell $Ca^{2+}$ currents appeared in the ApoCIII group (filled circles, n=26) in comparison with control group (open circles, n=26) or group subjected to incubation with ApoCIII in the presence of H-89 and PP2 (filled triangles, n=27) (FIG. 4D). Moreover, whole-cell $Ca^{2+}$ currents in control cells resembled those observed in cells treated with H-89 and PP2 (FIGS. 8C and D). The data reveal that ApoCIII enhances whole-cell $Ca^{2+}$ currents via coactivation of PKA and Src Kinase.

Apolipoprotein CIII does not Influence β Cell $Ca_V$1 Channel Expression

Overnight incubation with ApoCIII may influence β cell $Ca_V$1 channel expression. To test for this possibility, we analyzed β cell $Ca_V$1 channel expression in RINm5F cells following ApoCIII incubation. We found that anti-$Ca_V$1.2, anti-$Ca_V$1.3 and anti-GAPDH antibodies detected clear $Ca_V$1.2, $Ca_V$1.3 and GAPDH immunoreactive bands, respectively. Control and ApoCIII-treated samples gave similar intensities of $Ca_V$1.2, $Ca_V$1.3 and GAPDH immunoreactivities (Figure SA). FIG. 5B shows that there was no significant difference in the relative abundance of $Ca_V$1.2 (hatched column, n=6) and $Ca_V$1.3 subunits (filled column, n=6) in RINm5F cell homogenates subjected to ApoCIII incubation in comparison with vehicle incubation (open column, n=6) (P>0.05). The data reveal that ApoCIII incubation did not alter β cell $Ca_V$1 channel expression at the protein level.

Figure 6:
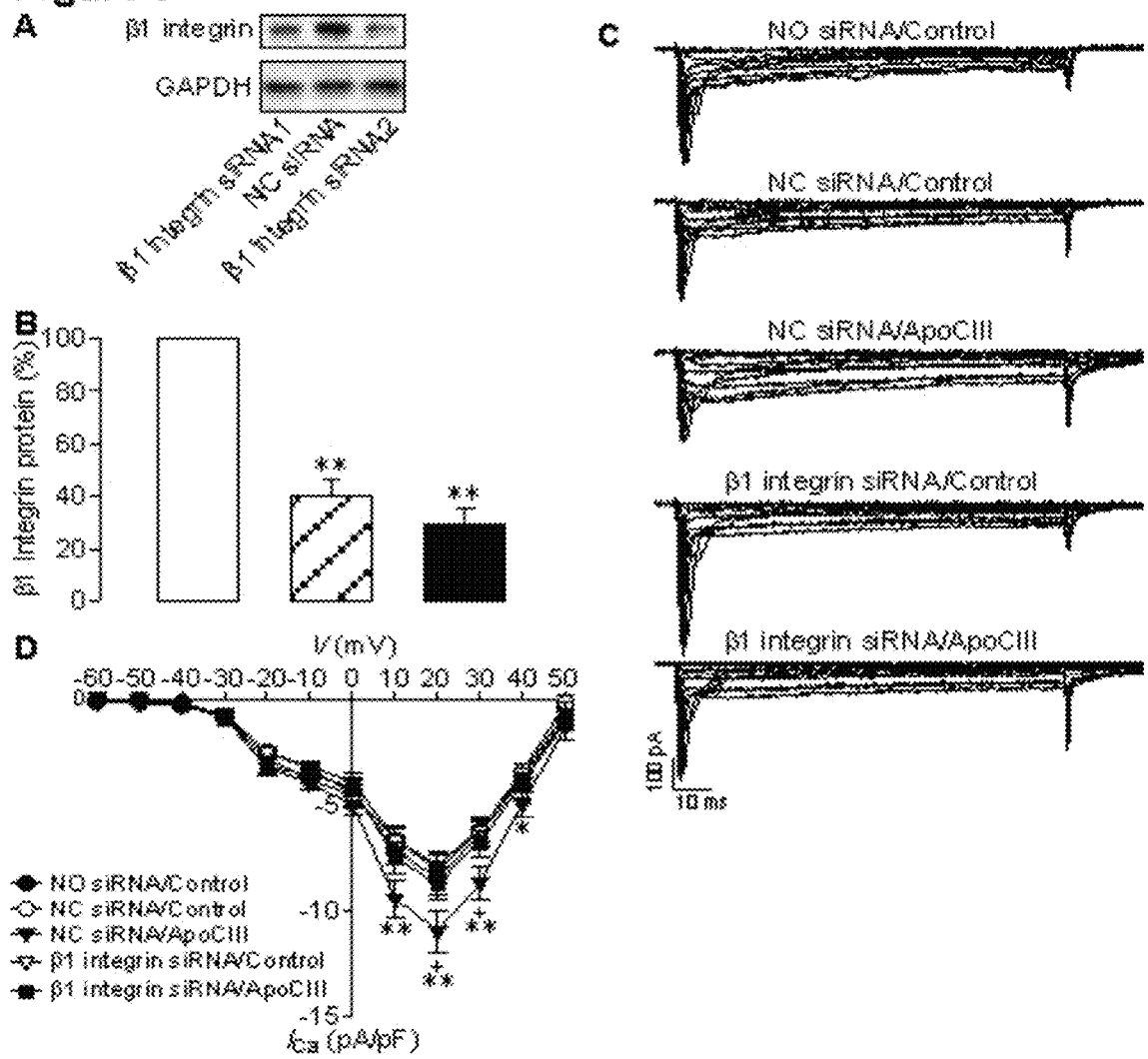
FIG. 6. Knockdown of β1 integrin abrogates apolipoprotein CIII-induced enhancement of whole-cell $Ca^{2+}$ currents in RINm5F cells. (A) Representative blots of β1 integrin- and GAPDH-immunoreactive bands in β1 integrin siRNA #1−, negative control siRNA (NC siRNA)- and β1 integrin siRNA #2-transfected cells. (B) Immunoblot quantifications of β1 integrin protein in NC siRNA-(open column, n=6), β1 integrin siRNA #1-(hatched column, n=6) and β1 integrin siRNA #2-transfected RINm5F cells (filled column, n=6). **P<0.01 versus NC siRNA. (C) Sample whole-cell $Ca^{2+}$ current traces registered in individual cells following mock transfection and incubation with control vehicle (NO siRNA/Control, cell capacitance: 12.1 pF), NC siRNA transfection and control vehicle treatment (NC siRNA/Control, cell capacitance: 11.4 pF), NC siRNA transfection and apolipoprotein CIII (ApoCIII) incubation (NC siRNA/ApoCIII, cell capacitance: 12.1 pF), β1 integrin siRNA transfection and exposure to vehicle solution β1 integrin siRNA/Control, cell capacitance: 11.9 pF) and β1 integrin siRNA transfection and ApoCIII exposure (β1 integrin siRNA/ApoCIII, cell capacitance: 12.4 pF), respectively. (D) $Ca^{2+}$ current density-voltage relationships in cells subjected to NO siRNA/Control (filled circles, n=29), NC siRNA/Control (open circles, n=28), NC siRNA/apoCIII (filled triangles, n=28), β1 integrin siRNA/Control (open triangles, n=29) and β1 integrin siRNA/ApoCIII (filled squares, n=29). *P<0.05 and **P<0.01 versus NO siRNA/Control, NC siRNA/Control and 31 integrin siRNA/Control. *P<0.05 versus 131 integrin siRNA/ApoCIII.

Apolipoprotein CIII Upregulates β Cell $Ca_V$ Channels Via β1 Integrin β1 integrin has been verified to serve as a mediator between ApoCIII and a certain number of protein kinases including PKA and Src kinase (Gui et al., 2006; Kawakami et al., 2006; Rueckschloss and Isenberg, 2004; Waitkus-Edwards et al., 2002; Wu et al., 2001). This together with our results that ApoCII hyperactivated β cell $Ca_V$ channels via coactivation of PKA and Src kinase raises the possibility for β1 integrin to mediate ApoCIII-induced hyperactivation of β cell $Ca_V$ channels. We investigated this possibility by implementing RNA interference in combination with whole-cell $Ca^{2+}$ analysis in RINm5F cells. It turned out that transfection with two β1 integrin siRNAs significantly decreased β1 integrin expression at the protein level (FIGS. 6A and B). We also visualized that whole-cell $Ca^{2+}$ currents detected in cells subjected to negative control siRNA transfection and ApoCIII exposure (NC siRNA/apoCIII) were larger than those in other cells following different treatments (FIG. 6C). These treatments included mock transfection and control vehicle incubation (NO siRNA/Control), negative control siRNA transfection and exposure to control vehicle (NC siRNA/Control), β1 integrin siRNA transfection and treatment with vehicle solution β1 integrin siRNA/Control), and β1 integrin siRNA transfection and ApoCIII incubation (β1 integrin siRNA/ApoCIII). Cells subsequent to NC siRNA/apoCIII (filled triangles, n=28) showed a significant increase in $Ca^{2+}$ current density at the voltage range 10-40 mV in comparison with NO siRNA/Control (n=29), NC siRNA/Control (n=28), β1 integrin siRNA/Control (n=29), and β1 integrin siRNA/ApoCIII (n=29) (FIG. 6D). The difference in $Ca^{2+}$ current density between NC siRNA/apoCIII and β1 integrin siRNA/apoCIII was less than that between NC siRNA/apoCIII and other treatments (FIG. 6D). Taken together, the results demonstrate that ApoCIII critically relies on β1 integrin to hyperactivate β cell $Ca_V$ channels.

DISCUSSION

The gross conductivity of $Ca_V$ channels depends on the density and activity of functional channels in the plasma membrane of the cell. Enhancement of whole-cell $Ca^{2+}$ currents by type 1 diabetic serum and its factor ApoCIII can result from enriched density and/or increased conductivity of functional $Ca_V$ channels in the β cell plasma membrane (Juntti-Berggren et al., 1993; Juntti-Berggren et al., 2004). However, all studies (Juntti-Berggren et al., 2004; Ristic et al., 1998; Yang and Berggren, 2005; Yang and Berggren, 2006) except one (Juntti-Berggren et al., 1993) have so far examined the effect of type 1 diabetic serum on $Ca_V$ channels only at the whole cell level. In the study by Juntti-Berggren et al, the increase in β cell $Ca_V$ channel activity by type 1 diabetic serum was characterized at both the single channel and the whole-cell level (Juntti-Berggren et al., 1993). Unfortunately, this work did not analyze whether type 1 diabetic serum could alter the density of functional $Ca_V$ channels in the β cell plasma membrane (Juntti-Berggren et al., 1993). Although we have previously revealed that ApoCIII serves as a type 1 diabetic serum factor, hyperactivating β cell $Ca_V$ channels, only whole-cell patch-clamp analysis was performed (Juntti-Berggren et al, 2004). Undoubtedly, detailed examination of biophysical properties of single $Ca_V$ channels in ApoCIII-treated cells should be implemented to mechanistically dissect hyperactivation of θ cell $Ca_V$ channels by this apolipoprotein. Interestingly, cell-attached single channel recordings in the present work reveals that incubation with ApoCIII not only augments the activity of individual β cell $Ca_V1$ channels but also enriches the number of functional $Ca_V1$ channels in the recorded area of the β cell plasma membrane. The augmentation of single $Ca_V1$ channel activity is visualized as an increased open probability attributed to the prolonged mean open time and shortened mean closed time. Enrichment of number of functional $Ca_V1$ channels is verified by appearance of more levels of single $Ca_V1$ channel conductance.

The insulin-secreting RINm5F cell is equipped with $Ca_V1$, $Ca_V2$ and $Ca_V3$ channels (Yang and Berggren, 2005; Yang and Berggren, 2006). We investigated if ApoCIII selectively hyperactivates $Ca_V1$ channels or indiscriminately impacts all these three types of $Ca_V$ channels in this insulin-secreting cell. It turned out that ApoCIII-induced hyperactivation of β cell $Ca_V$ channels could no longer take place following pharmacological ablation of $Ca_V1$ channels. This means that ApoCII selectively hyperactivates $Ca_V1$ channels, which are the major $Ca_V$ channel type playing a predominant role over other types of $Ca_V$ channels in β cell physiology and pathophysiology. The selective hyperactivation of β cell $Ca_V1$ channels by ApoCIII accounts for the pathophysiological role of this lipoprotein in $Ca^{2+}$-dependent β cell death (Juntti-Berggren et al., 2004; Yang and Berggren, 2005; Yang and Berggren, 2006).

A series of protein kinases, such as PKA and PKC, can effectively phosphorylate $Ca_V$ channels resulting in increases in the open channel density and activity due to phosphorylation-induced conformational changes in these channels (Catterall, 2000; Kavalali et al., 1997; Yang and Tsien, 1993). Increases in the number and open probability of functional $Ca_V$ channels by ApoCIII might be mediated by protein kinases. ApoCIII has been demonstrated to activate PKC through β1 integrin in monocytic cells (Kawakami et al., 2006). Furthermore, β1 integrin activation can also upregulate $Ca_V1$ channels in neurons, ventricular myocytes and vascular smooth muscle cells through stimulation of PKA, PKC and Src kinase (Gui et al., 2006; Rueckschloss and Isenberg, 2004; Waitkus-Edwards et al., 2002; Wu et al., 2001). All these components are present in β cells (Bosco et al., 2000; Kantengwa et al., 1997; Mukai et al., 2011; Nikolova et al., 2006; Yang and Berggren, 2006) and may suggest that ApoCIII employs the β1 integrin-PKA/PKC/Src kinase cascade to hyperactivate 13 cell $Ca_V$ channels. Indeed, the present work shows that complex inhibition of PKA, PKC and Src kinase effectively abrogates ApoCIII-induced hyperactivation of β cell $Ca_V$ channels and that coinhibition of PKA and Src kinase is enough for this effect. However, individual inhibition of PKA, PKC or Src kinase only produced, if anything, a marginal effect on ApoCIII-induced hyperactivation of β cell $Ca_V$ channels. Hence, we conclude that ApoCIII relies on parallel PKA and Src pathways to upregulate β cell $Ca_V$ channels.

Occurrence of ApoCIII-induced hyperactivation of β cell $Ca_V$ channels requires overnight incubation. Hence, the effect might be accounted for by an increase in $Ca_V$ channel expression. Therefore, we quantified immunoreactivities of $Ca_V1.2$ and $Ca_V1.3$ subunits in RINm5F cells following overnight incubation with ApoCIII. However, the incubation had no influence on β cell $Ca_V1$ channel expression. We therefore excluded the possibility that ApoCIII elevates β cell $Ca_V1$ channel expression.

The transmembrane receptor β1 integrin is noncovalently associated with other integrins to form a set of heterodimers. They recognize a large number of soluble and surface-bound proteins to mediate cell-cell, cell-extracellular matrix and cell-pathogen interactions (Luo et al., 2007). β1 Integrin is situated downstream of ApoCIII and upstream of PKA/PKC/Src kinase in some cell types (Gui et al., 2006; Kawakami et al., 2006; Rueckschloss and Isenberg, 2004; Waitkus-Edwards et al., 2002; Wu et al., 2001). This made us investigate whether the ApoCIII-β1 integrin-PKA/PKC/Src kinase pathway operates in the β cell as the mechanism whereby this apolipoprotein hyperactivates $Ca_V1$ channels. Interestingly, knockdown of β1 integrin does not influence β cell $Ca_V$ channel activity in the absence of ApoCIII, but significantly abrogates ApoCIII-induced hyperactivation of β cell $Ca_V$ channels. The results clearly verify that β1 integrin plays a significant role in mediating the action of ApoCIII on β cell $Ca_V1$ channel activity.

In conclusion, our findings demonstrate that ApoCIII selectively hyperactivates β cell $Ca_v1$ channels through parallel PKA and Src kinase pathways in a β1 integrin-dependent fashion. ApoCIII-induced hyperactivation of β cell $Ca_v1$ channels is characterized by the enriched density and increased activity of functional $Ca_v1$ channels in the β cell plasma membrane. Undoubtedly, this novel signal-transduction pathway has a potential to serve as an innovative drug discovery platform for the prevention of $Ca^{2+}$-dependent β cell death in association with diabetes.

EXPERIMENTAL PROCEDURES

Cell Culture and Treatments

Islets of Langerhans were isolated from adult male and female mice and dispersed into single (3 cells. RINm5F cells at about 70% confluency were trypsinized. The resultant suspension of cells was seeded into Petri dishes or 12-well plates. The cells were cultivated in RPMI 1640 medium supplemented with 10% fetal bovine serum, 2 mM L-glutamine, and 100 U/100 g/ml penicillin/streptomycin (Invitrogen, Carlsbad, Calif.) and maintained at 37° C. in a humidified 5% $CO_2$ incubator. They were grown overnight and then subjected to siRNA transfection. For patch-clamp analysis, cells underwent overnight treatment with ApoCIII, the PKA inhibitor H-89 (Calbiochem, La Jolla, Calif.), the PKC inhibitor calphostin C (Calbiochem), the Src kinase inhibitor PP2 (Calbiochem) and the $Ca_v1$ channel blocker nimodipine (Calbiochem) in RPMI medium at final concentrations of 20 μg/ml, 0.5 μM, 0.1 μM, 0.1 μM and 5 μM, respectively. ApoCIII was dissolved in 0.1% triflouroacetic acid (TFA) to make a stock solution of 1 mg/ml, whereas H-89, calphostin C, PP2 and nimodipine were dissolved in dimethyl sulfoxide (DMSO) to form stock solutions of 5 mM, 1 mM, 1 mM and 10 mM, respectively. 0.002% TFA and/or 0.03% DMSO were used as vehicle controls.

siRNA Design and Transfection

Two pairs of 21-mer siRNA duplexes targeting the rat β1 integrin (β1 integrin siRNA #1, ID127971 and β1 integrin siRNA #2, ID127972) were designed and chemically synthesized by Applied Biosystems/Ambion (Austin, Tex.). Their sequences were subjected to BLAST search to ensure their specificity. Silencer® Select Negative Control siRNA (4390843), not targeting any gene product, and Silencer® Select GAPDH Positive Control siRNA (4390849), efficiently silencing GAPDH in human, mouse, and rat cells, were purchased from Applied Biosystems/Ambion (Austin, Tex.). RINm5F cells were reversely transfected with Lipofectamine™ RNAiMAX™. Briefly, negative control siRNA, β1 integrin siRNA #1 or β1 integrin siRNA #2 was mixed with Lipofectamine™ RNAiMAX™ followed by 20-min incubation at room temperature. Subsequently, cells were added to the siRNA/Lipofectamine™ RNAiMAX mixtures followed by gentle agitation and kept at 37° C. in a humidified 5% $CO_2$ incubator. After 72 h, the transfected cells were grown to about 70% confluency and subjected to immunoblot assay or different treatments.

SDS-PAGE and Immunoblot Analysis

RINm5F cells following different treatments were lysed in a lysis buffer (pH 7.5) consisting of 50 mM HEPES, 150 mM NaCl, 1 mM EGTA, 1 mM EDTA, 10% glycerol, 1% triton X-100, 1 mM PMSF and a protease inhibitor cocktail (Roche Diagnostics, Mannheim, Germany). The lysate was centrifuged at 800×g for 10 min at 4° C. to remove cell debris and nuclei. The protein concentration of the resulting samples was determined with Bio-Rad protein assay reagent (Bio-Rad, Hercules, Calif.). The samples were then denatured by heating at 96° C. for 3 min in SDS sample buffer and underwent sodium dodecyl sulfate-polyacrylamide gel electrophoresis (SDS-PAGE) and immunoblot analysis. Briefly, 50, 90 or 180 μg proteins were separated in discontinuous gels consisting of a 4% acrylamide stacking gel (pH 6.8) and an 8% acrylamide separating gel (pH 8.8). The separated proteins were then electroblotted to hydrophobic polyvinylidene difluoride membrane (Hybond-P; GE Healthcare, Uppsala, Sweden). The blots were blocked by incubation for 1 h with 5% non-fat milk powder in a washing buffer, containing 50 mM tris(hydroxymethyl)aminomethane, 150 mM NaCl and 0.05% Tween 20 (pH 7.5). They were then incubated overnight at 4° C. with affinity-purified rabbit polyclonal antibodies to β1 integrin (1:500; Millipore, Billerica, Mass.), $Ca_v1.2$ (1:200) and $Ca_v1.3$ (1:200), respectively, and for 1 h at room temperature with mouse monoclonal antibody to glyceraldehyde-3-phosphate dehydrogenase (GAPDH, 1:4000; Applied Biosystems/Ambion, Austin, Tex.), respectively. After rinsing with the washing buffer, the blots were incubated with the secondary antibodies (either horseradish peroxidase-conjugated goat anti-rabbit IgG or horseradish peroxidase-conjugated goat anti-mouse IgG; 1:50,000; Bio-Rad, Hercules, Calif.) at room temperature for 45 min. The immunoreactive bands were visualized with the ECL plus Western blotting detection system (GE Healthcare, Uppsala, Sweden).

Electrophysiology

Mouse islet cells and RINm5F cells following different treatments were subjected to single channel and whole-cell patch-clamp measurements. Cell-attached and perforated whole-cell patch-clamp configurations were employed. Electrodes were made from borosilicate glass capillaries, fire-polished and coated with Sylgard close to their tips. Some of them were filled with a solution containing (in mM) 110 $BaCl_2$, 10 TEA-Cl, and 5 HEPES (pH 7.4 with $Ba(OH)_2$) for single channel measurements. Others were filled with a solution composed of (in mM) 76 $Cs_2SO_4$, 1 $MgCl_2$, 10 KCl, 10 NaCl, and 5 HEPES (pH 7.35 with CsOH), as well as amphotericin B (0.24 mg/ml) for whole-cell current recordings. Electrode resistance ranged between 4 and 6 MΩ when they were filled with electrode solutions and immersed in bath solutions. The electrode offset potential was corrected in bath solutions prior to gigaseal formation. Single-channel recordings were performed with cells bathed in a depolarizing external recording solution, containing (in mM) 125 KCl, 30 KOH, 10 EGTA, 2 $CaCl_2$, 1 $MgCl_2$, and 5 HEPES-KOH (pH 7.15). This solution was used to bring the intracellular potential to 0 mV. For perforated whole-cell current measurements, the cells were bathed in a solution containing (in mM) 138 NaCl, 5.6 KCl, 1.2 $MgCl_2$, 10 $CaCl_2$, 5 HEPES (pH 7.4). Single channel and whole-cell currents were recorded with an Axopatch 200B amplifier (Molecular Devices, Foster City, Calif.) and an EPC-9 patch clamp amplifier (HEKA Elektronik, Lambrecht/Pfalz, Germany), respectively, at room temperature (about 22° C.). Acquisition and analysis of single channel and whole-cell current data were done using the software program pCLAMP 10 (Axon Instruments) and the software program PatchMaster/FitMaster (HEKA), respectively. The amplitude of whole-cell currents was normalized by the cell capacitance.

Statistical Analysis

All data are presented as mean±SEM. Statistical significance was determined by one-way ANOVA, followed by least significant difference (LSD) test. When two groups were compared, unpaired Student's t test or Mann-Whitney U test was employed. The significance level was set at 0.05 or 0.01.

REFERENCES FOR EXAMPLE 1

Atzmon, G., Rincon, M., Schechter, C. B., Shuldiner, A. R., Lipton, R. B., Bergman, A., and Barzilai, N. (2006). Lipoprotein genotype and conserved pathway for exceptional longevity in humans. PLoS Biol. 4, e113.

Bosco, D., Meda, P., Halban, P. A., and Rouiller, D. G. (2000). Importance of cell-matrix interactions in rat islet R-cell secretion in vitro: role of $\alpha 6\beta 1$ integrin. Diabetes 49, 233-243.

Catterall, W. A. (2000). Structure and regulation of voltage-gated $Ca^{2+}$ channels. Annu. Rev. Cell Dev. Biol. 16, 521-555.

Chan, D. C., Watts, G. F., Redgrave, T. G., Mori, T. A., and Barrett, P. H. (2002). Apolipoprotein B-100 kinetics in visceral obesity: associations with plasma apolipoprotein C-III concentration. Metabolism 51, 1041-1046.

Clavey, V., Lestavel-Delattre, S., Copin, C., Bard, J. M., and Fruchart, J. C. (1995). Modulation of lipoprotein B binding to the LDL receptor by exogenous lipids and apolipoproteins CI, CII, CIII, and E. Arterioscler. Thromb. Vasc. Biol. 15, 963-971.

Fang, D. Z., and Liu, B. W. (2000). Apolipoprotein C-Ill can specifically bind to hepatic plasma membranes. Mol. Cell. Biochem. 207, 57-64.

Gangabadage, C. S., Zdunek, J., Tessari, M., Nilsson, S., Olivecrona, G., and Wijmenga, S. S. (2008). Structure and dynamics of human apolipoprotein CIII. J. Biol. Chem. 283, 17416-17427.

Gui, P., Wu, X., Ling, S., Stotz, S. C., Winkfein, R. J., Wilson, E., Davis, G. E., Braun, A. P., Zamponi, G. W., and Davis, M. J. (2006). Integrin receptor activation triggers converging regulation of Cav1.2 calcium channels by c-Src and protein kinase A pathways. J. Biol. Chem. 281, 14015-14025.

Huard, K., Bourgeois, P., Rhainds, D., Falstrault, L., Cohn, J. S., and Brissette, L. (2005). Apolipoproteins C-II and C-III inhibit selective uptake of low- and high-density lipoprotein cholesteryl esters in HepG2 cells. Int. J. Biochem. Cell Biol. 37, 1308-1318.

Jong, M. C., Hofker, M. H., and Havekes, L. M. (1999). Role of ApoCs in lipoprotein metabolism: functional differences between ApoC1, ApoC2, and ApoC3. Arterioscler. Thromb. Vasc. Biol. 19, 472-484.

Juntti-Berggren, L., Larsson, O., Rorsman, P., Ammala, C., Bokvist, K., Wahiander, K., Nicotera, P., Dypbukt, J., Orrenius, S., Hallberg, A., et al. (1993). Increased activity of L-type $Ca^{2+}$ channels exposed to serum from patients with type I diabetes. Science 261, 86-90.

Juntti-Berggren, L., Refai, E., Appelskog, I., Andersson, M., Imreh, G., Dekki, N., Uhles, S., Yu, L., Griffiths, W. J., Zaitsev, S., et al. (2004). Apolipoprotein CIII promotes $Ca^{2+}$-dependent $\beta$ cell death in type 1 diabetes. Proc. Natl. Acad. Sci. USA 101, 10090-10094.

Kantengwa, S., Baetens, D., Sadoul, K., Buck, C. A., Halban, P. A., and Rouiller, D. G. (1997). Identification and characterization of $\alpha 3\beta 1$ integrin on primary and transformed rat islet cells. Exp. Cell Res. 237, 394-402.

Kato, S., Ishida, H., Tsuura, Y., Tsuji, K., Nishimura, M., Horie, M., Taminato, T., Ikehara, S., Odaka, H., Ikeda, H., et al. (1996). Alterations in basal and glucose-stimulated voltage-dependent $Ca^{2+}$ channel activities in pancreatic $\beta$ cells of non-insulin-dependent diabetes mellitus G K rats. J. Clin. Invest. 97, 2417-2425.

Kawakami, A., Aikawa, M., Libby, P., Alcaide, P., Luscinskas, F. W., and Sacks, F. M. (2006). Apolipoprotein CIII in apolipoprotein B lipoproteins enhances the adhesion of human monocytic cells to endothelial cells. Circulation 113, 691-700.

Kawakami, A., Aikawa, M., Nitta, N., Yoshida, M., Libby, P., and Sacks, F. M. (2007). Apolipoprotein CIII-induced THP-1 cell adhesion to endothelial cells involves pertussis toxin-sensitive G protein- and protein kinase Ca-mediated nuclear factor-κB activation. Arterioscler. Thromb. Vasc. Biol. 27, 219-225.

Kavalali, E. T., Hwang, K. S., and Plummer, M. R. (1997). cAMP-dependent enhancement of dihydropyridine-sensitive calcium channel availability in hippocampal neurons. J. Neurosci. 17, 5334-5348.

Luo, B. H., Carman, C. V., and Springer, T. A. (2007). Structural basis of integrin regulation and signaling. Annu. Rev. Immunol. 25, 619-647.

Mukai, E., Fujimoto, S., Sato, H., Oneyama, C., Kominato, R., Sato, Y., Sasaki, M., Nishi, Y., Okada, M., and Inagaki, N. (2011). Exendin-4 suppresses Src activation and reactive oxygen species production in diabetic Goto-Kakizaki rat islets in an Epac-dependent manner. Diabetes 60, 218-226.

Nikolova, G., Jabs, N., Konstantinova, I., Domogatskaya, A., Tryggvason, K., Sorokin, L., Fassler, R., Gu, G., Gerber, H. P., Ferrara, N., et al. (2006). The vascular basement membrane: a niche for insulin gene expression and $\beta$ cell proliferation. Dev. Cell 10, 397-405.

Ristic, H., Srinivasan, S., Hall, K. E., Sima, A. A., and Wiley, J. W. (1998). Serum from diabetic BB/W rats enhances calcium currents in primary sensory neurons. J. Neurophysiol. 80, 1236-1244.

Rueckschloss, U., and Isenberg, G. (2004). Contraction augments L-type $Ca^{2+}$ currents in adherent guinea-pig cardiomyocytes. J. Physiol. 560, 403-411.

Sol, E. M., Sundsten, T., and Bergsten, P. (2009). Role of MAPK in apolipoprotein CIII-induced apoptosis in INS-1E cells. Lipids Health Dis. 8, 3.

Sundsten, T., Ostenson, C. G., and Bergsten, P. (2008). Serum protein patterns in newly diagnosed type 2 diabetes mellitus—influence of diabetic environment and family history of diabetes. Diabetes Metab. Res. Rev. 24, 148-154.

Waitkus-Edwards, K. R., Martinez-Lemus, L. A., Wu, X., Trzeciakowski, J. P., Davis, M. J., Davis, G. E., and Meininger, G. A. (2002). $\alpha_4\beta_1$ Integrin activation of L-type calcium channels in vascular smooth muscle causes arteriole vasoconstriction. Circ. Res. 90, 473-480.

Wu, X., Davis, G. E., Meininger, G. A., Wilson, E., and Davis, M J. (2001). Regulation of the L-type calcium channel by $\alpha_5\beta_1$ integrin requires signaling between focal adhesion proteins. J. Biol. Chem. 276, 30285-30292.

Xu, S., Laccotripe, M., Huang, X., Rigotti, A., Zannis, V. I., and Krieger, M. (1997). Apolipoproteins of HDL can directly mediate binding to the scavenger receptor SR-BI, an HDL receptor that mediates selective lipid uptake. J. Lipid Res. 38, 1289-1298.

Yang, J., and Tsien, R. W. (1993). Enhancement of N- and L-type calcium channel currents by protein kinase C in frog sympathetic neurons. Neuron 10, 127-136.

Yang, S. N., and Berggren, P. O. (2005). $\beta$-Cell $Ca_V$ channel regulation in physiology and pathophysiology. Am. J. Physiol. 288, E16-E28.

Yang, S. N., and Berggren, P. O. (2006). The role of voltage-gated calcium channels in pancreatic $\beta$-cell physiology and pathophysiology. Endocr. Rev. 27, 621-676.

We claim:

1. A method for treating or limiting development of diabetes, comprising administering to a subject in need thereof an amount effective of an anti-β1 integrin antibody to treat or limit development of diabetes.

2. The method of claim 1, wherein the method is for treating diabetes.

3. The method of claim 1, wherein the method is for limiting development of diabetes.

4. The method of claim 1, wherein the subject has or is at risk of developing type 1 diabetes.

5. The method of claim 1, wherein the subject has or is at risk of developing type 2 diabetes.

6. The method of claim 1, wherein the subject has type 2 diabetes.

7. The method of claim 1, wherein the subject overexpresses apoCIII relative to control.

8. The method of claim 2, wherein the subject overexpresses apoCIII relative to control.

9. The method of claim 3, wherein the subject overexpresses apoCIII relative to control.

10. The method of claim 4, wherein the subject overexpresses apoCIII relative to control.

11. The method of claim 5, wherein the subject overexpresses apoCIII relative to control.

12. The method of claim 6, wherein the subject overexpresses apoCIII relative to control.

* * * * *